United States Patent [19]

Auerbach

[11] Patent Number: 5,354,668

[45] Date of Patent: Oct. 11, 1994

[54] METHODS FOR THE ISOTHERMAL AMPLIFICATION OF NUCLEIC ACID MOLECULES

[76] Inventor: Jeffrey I. Auerbach, 13109 Jasmine Hill Terr., Rockville, Md. 20850

[21] Appl. No.: 136,405

[22] Filed: Oct. 15, 1993

Related U.S. Application Data

[63] Continuation of Ser. No. 933,945, Aug. 24, 1992, abandoned, which is a continuation-in-part of Ser. No. 924,643, Aug. 4, 1992, abandoned.

[51] Int. Cl.⁵ .................... C12Q 1/68; C12P 19/34
[52] U.S. Cl. ........................ 435/91.1; 435/6
[58] Field of Search .................... 435/6, 91.1

[56] References Cited

U.S. PATENT DOCUMENTS

| | | | |
|---|---|---|---|
| 4,582,788 | 4/1986 | Erlich | 435/6 |
| 4,673,640 | 6/1987 | Backman | 435/68 |
| 4,683,194 | 7/1987 | Saiki et al. | 435/6 |
| 4,683,202 | 7/1987 | Mullis | 435/91 |
| 4,959,317 | 9/1990 | Sauer | 435/172.3 |

FOREIGN PATENT DOCUMENTS

| | | | |
|---|---|---|---|
| 329822 | 8/1989 | European Pat. Off. | C12Q 1/68 |
| 427074 | 5/1991 | European Pat. Off. | |
| WO88/10315 | 12/1988 | PCT Int'l Appl. | C12Q 1/68 |
| WO89/06700 | 7/1989 | PCT Int'l Appl. | C12Q 1/68 |

OTHER PUBLICATIONS

Bellofatto, et al. Generation of a Tn5 promoter probe and its use in the study of gene expression . . . Proc. Natl. Acad Sci. USA (Feb. 1984) 81:1035–39.
Mullis et al., "Specific Enzymatic Amplification of DNA in Vitro: The Polymerase Chain Reaction," *Cold Spring Harbor Symp. Quant. Biol.* 51:263–273 (1986).
Higuchi, "Using PCR to Engineer DNA," In: *PCR Technology*, Ehrlich, H. (ed.), Stockton Press, N.Y., 1989, pp. 61–68.
Hoess, R. et al., "The Nature of the Interaction of the P1 Recombinase Cre with the Recombining Site loxP," *Cold Spring Harbor. Symp. Quant. Biol.* 49:761–768 (1984).
Hamilton, D. L. et al., "Site-Specific Recombination by the Bacteriophage P1 loxP-Cre System," *J. Molec. Biol.* 178:481–486 (1984).
Sauer, B. "Functional Expression of the cre–lox Site-Specific Recombination System in the Yeast Saccharomyces cerevisiae," *Molec. Cell. Biol.* 7:2087–2096 (1987).
Sauer, B. et al. "Site-Specific DNA Recombination in Mammalian Cells by the Cre Recombinase of Bacteriophage P1," *Proc. Natl. Acad. Sci. (U.S.A.)* 85:5166–5170 (1988).
Abremski, K. et al., "Studies on the Properties of P1 Site-Specific Recombination: Evidence for Topologically Unlinked Products Following Recombination," *Cell* 32:1301–1311 (1983).
Hoess, R. et al., "P1 Site-Specific Recombination: Nucleotide Sequence of the Recombining Sites," *Proc. Natl. Acad. Sci. (U.S.A.)* 79:3398–3402 (1982).
Sternberg, N. et al., "Site-Specific Recombination and Its Role in the Life Cycle of Bacteriophage P1," *Cold Spring Harbor Symp. Quant. Biol.* 45:297–309 (1981).
Hoess, R. et al., "Interaction of the Bacteriophage P1 Recombinase Cre with the Recombining Site loxP," *Proc. Natl. Acad. Sci. (U.S.A.)* 81:1026–1029 (1984).
Abremski, K. et al., "Bacteriophage P1 Site-Specific Recombination: Purification and Properties of the Cre Recombinase Protein," *J. Molec. Biol.* 259:1509–1514 (1984).
Abremski, K. et al., "Bacteriophage P1 Cre–loxP Site-Specific Recombination: Site-Specific DNA Topoisomerase Activity of the Cre Recombination Protein," *J. Biol. Chem.* 261:391–396 (1986).
Sauer, B. et al., "Site-Specific Insertion of DNA into a Pseudorabies Virus Vector," *Proc. Natl. Acad. Sci. (U.S.A.)* 84:9108–9112 (1987).
Palazzolo, M. J. et al., "Phage Lambda cDNA Cloning Vectors for Subtractive Hybridization, Fusion-Protein Synthesis and Cre-loxP Automatic Plasmid Subcloning," *Gene* 88:25–36 (1990).
Kwoh D. et al., "Transcription-Based Amplification System and Detection of Amplified Human Immunodeficiency Virus Type 1 with a Bead-Based Sandwich Hybridization Assay," *Proc. Natl. Acad. Sci. (U.S.A.)* 86:1173 (1989).
Ohara, O. et al., "One-sided Polymerase Chain Reaction: The Amplification of cDNA," *Proc. Natl. Acad. Sci. (U.S.A.)* 86:5673–5677 (1989).

Frohman, M. A., "RACE: Rapid Analysis of cDNA Ends," In: *PCR Protocols: A Guide to Methods and Applications* Academic Press, N.Y. (1990).

Wu, D. Y. et al., "The Ligation Amplification Reaction (LAR)–Amplification of Specific DNA Sequences Using Sequential Rounds of Template–Dependent Ligation," *Genomics* 4:560 (1989).

Mullis, K. B. et al., "Specific Synthesis of DNA in Vitro via a Polymerase–Catalyzed Chain Reaction," In: *Met. Enzymol.* 155:335–350 (1987).

Walker, G. T. et al., "Isothermal in vitro Amplification of DNA by a Restriction Enzyme/DNA Polymerase System," *Proc. Natl. Acad. Sci. (U.S.A.)* 89:392–396 (1992).

Chatterjee, D. K. et al., "Cloning and Overexpression of the Gene Encoding Bacteriophage T5 DNA Polymerase," *Gene* 97:13–19 (1991).

Gillin, F. et al., "Control of Mutation frequency by Bacteriophage T4 DNA Polymerase: I. The CB120 Antimutator DNA Polymerase is Defective in Strand Displacement," *J. Biol. Chem* 251:5219–5224 (1976).

Kolodner, R. et al., "Gene 4 Protein of Bacteriophage T7: Characterization of the Product Synthesized by the T7 DNA Polymerase and Gene 4 Protein in the Absence of Ribonucleoside 5'–Triphosphates," *J. Biol. Chem* 253:574–584 (1978).

Eki, T. et al., "Influence of Poly(ADP-ribose) Polymerase on the Enzymatic Synthesis of SV40 DNA," *J. Biol. Chem* 266:3087–3100 (1991).

Parada, C. et al., "Transcriptional activation of pBR322 DNA can lead to Duplex DNA Unwinding Catalyzed by the Escherichia coli Preprimosome," *J. Biol. Chem* 264:15120–15129 (1989).

*Primary Examiner*—Margaret Parr
*Assistant Examiner*—David Schreiber

[57] ABSTRACT

Methods for amplifying a nucleic acid molecule which employs a single primer, and in which the amplification is performed under isothermal conditions. The invention also includes kits containing reagents for conducting the method.

22 Claims, 14 Drawing Sheets

A

B

C

D or or

METHODS FOR THE ISOTHERMAL AMPLIFICATION OF NUCLEIC ACID MOLECULES

CROSS-REFERENCE TO RELATED APPLICATIONS

This application is a continuation of U.S. patent application Ser. No. 07/933,945, filed Aug. 24, 1992, now abandoned, which application was a continuation-in-part of U.S. patent application Ser. No. 07/924,643, filed Aug. 4, 1992.

FIELD OF THE INVENTION

The present invention is in the field of recombinant DNA technology. This invention is directed to a process for amplifying a nucleic acid molecule, and to the molecules employed and produced through this process.

BACKGROUND OF THE INVENTION

Assays capable of detecting the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

The usefulness of a detection assay is often limited by the concentration at which a particular target nucleic acid molecule is present in a sample. Thus, methods that are capable of amplifying the concentration of a nucleic acid molecule have been developed as adjuncts to detection assays.

One method for overcoming the sensitivity limitation of nucleic acid concentration is to selectively amplify the nucleic acid molecule whose detection is desired prior to performing the assay. Recombinant DNA methodologies capable of amplifying purified nucleic acid fragments in vivo have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

In many instances in clinical medicine and diagnostics, however, the concentration of a target species in a sample under evaluation is so low that it cannot be readily cloned. To address such situations, methods of in vitro nucleic acid amplification have been developed that employ template directed extension. In such methods, the nucleic acid molecule is used as a template for extension of a nucleic acid primer in a reaction catalyzed by polymerase.

One such template extension method is the "polymerase chain reaction" ("PCR"), which is among the most widely used methods of DNA amplification (Mullis, K. et al., *Cold Spring Harbor Symp. Quant. Biol.* 51:263-273 (1986); Erlich H. et al., EP 50,424; EP 84,796, EP 258,017, EP 237,362; Mullis, K., EP 201,184; Mullis K. et al., U.S. Pat. Nos. 4,683,202; Erlich, H., 4,582,788; Saiki, R. et al., 4,683,194 and Higuchi, R. "PCR Technology," Ehrlich, H. (ed.), Stockton Press, N.Y., 1989, pp 61–68), which references are incorporated herein by reference).

The polymerase chain reaction can be used to selectively increase the concentration of a nucleic acid molecule even when that molecule has not been previously purified and is present only in a single copy in a particular sample. The method can be used to amplify either single- or double-stranded DNA. The essence of the method involves the use of two oligonucleotides to serve as primers for the template-dependent, polymerase mediated replication of the desired nucleic acid molecule.

The precise nature of the two oligonucleotide primers of the PCR method is critical to the success of the method. As is well known, a molecule of DNA or RNA possesses directionality, which is conferred through the $5' \rightarrow 3'$ linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a 5' nucleoside triphosphate to the 3' hydroxyl end of a nucleic acid molecule. Thus, the action of a polymerase extends the 3' end of a nucleic acid molecule. These inherent properties are exploited in the selection of the two oligonucleotide primers of the PCR. The oligonucleotide sequences of the two primers of the PCR method are selected such that they contain sequences identical to, or complementary to, sequences which flank the sequence of the particular nucleic acid molecule whose amplification is desired. More specifically, the nucleotide sequence of the "first" primer is selected such that it is capable of hybridizing to an oligonucleotide sequence located 3' to the sequence of the desired nucleic acid molecule that is to be amplified, whereas the nucleotide sequence of the "second" primer is selected such that it contains a nucleotide sequence identical to one present 5' to the sequence of the desired nucleic acid molecule that is to be amplified. Both primers possess the 3' hydroxyl groups which are necessary for enzyme mediated nucleic acid synthesis.

In the polymerase chain reaction, the reaction conditions must be cycled between those conducive to hybridization and nucleic acid polymerization, and those which result in the denaturation of duplex molecules. In the first step of the reaction, the nucleic acid molecules of the sample are transiently heated, and then cooled, in order to denature any double stranded molecules that may be present. The "first" and "second" primers are then added to the sample at a concentration which greatly exceeds that of the desired nucleic acid molecule. When the sample is then incubated under conditions conducive to hybridization and polymerization, the "first" primer will hybridize to the nucleic acid molecule of the sample at a position 3' to the sequence of the desired molecule to be amplified. If the nucleic acid molecule of the sample was initially double stranded, the "second" primer will hybridize to the complementary strand of the nucleic acid molecule at a position 3' to the sequence of the desired molecule that is the complement of the sequence whose amplification is desired. Upon addition of a polymerase, the 3' ends of the "first" and (if the nucleic acid molecule was double stranded) "second" primers will be extended. The extension of the "first" primer will result in the synthesis of a DNA molecule having the exact sequence of the complement of the desired nucleic acid. Extension of the "second" primer will result in the synthesis of a DNA molecule having the exact sequence of the desired nucleic acid.

The PCR reaction is capable of exponentially amplifying the desired nucleic acid sequences, with a near doubling of the number of molecules having the desired sequence in each cycle. This exponential increase occurs because the extension product of the "first" primer contains a sequence which is complementary to a sequence of the "second" primer, and thus can serve as a template for the production of an extension product of the "second" primer. Similarly, the extension product of the "second" primer, of necessity, contain a sequence which is complementary to a sequence of the "first" primer, and thus can serve as a template for the production of an extension product of the "first" primer. Thus, by permitting cycles of hybridization, polymerization, and denaturation, an exponential increase in the concentration of the desired nucleic acid molecule can be achieved. Reviews of the polymerase chain reaction are provided by Mullis, K. B. (*Cold Spring Harbor Symp. Quant. Biol.* 51:263–273 (1986)); Saiki, R. K., et al. (*Bio/Technology* :1008–1012 (1985)); and Mullis, K. B., et al. (*Met. Enzymol.* 155:335–350 (1987), which references are incorporated herein by reference).

PCR technology is useful in that it can achieve the rapid and extensive amplification of a polynucleotide molecule. However, the method has several salient deficiencies. First, it requires the preparation of two different primers which hybridize to two oligonucleotide sequences of the target sequence flanking the region that is to be amplified. The concentration of the two primers can be rate limiting for the reaction. Although it is not essential that the concentration of the two primers be identical, a disparity between the concentrations of the two primers can greatly reduce the overall yield of the reaction.

A further disadvantage of the PCR reaction is that when two different primers are used, the reaction conditions chosen must be such that both primers "prime" with similar efficiency. Since the two primers necessarily have different sequences, this requirement can constrain the choice of primers and require considerable experimentation. Furthermore, if one tries to amplify two different sequences simultaneously using PCR (i.e. using two sets of two primers), the reaction conditions must be optimized for four different primers.

A further disadvantage of PCR is that it requires the thermocycling of the molecules being amplified. Since this thermocycling requirement denatures conventional polymerases, it thus requires the addition of new polymerase at the commencement of each cycle. The requirement for additional polymerase increases the expense of the reaction, and can be avoided only through the use of thermostable polymerases, such as Taq polymerase. Moreover, the thermocycling requirement attenuates the overall rate of amplification because further extension of a primer ceases when the sample is heated to denature double-stranded nucleic acid molecules. Thus, to the extent that the extension of any primer molecule has not been completed prior to the next heating step of the cycle, the rate of amplification is impaired.

Other known nucleic acid amplification procedures include transcription-based amplification systems (Kwoh D. et al., *Proc. Natl. Acad. Sci.* (*U.S.A.*) 86:1173 (1989); Gingeras T. R. et al., PCT appl. WO 88/10315 (priority: U.S. patent application Ser. Nos. 064,141 and 202,978); Davey, C. et. al., European Patent Application Publication no. 329,822; Miller, H. I. et al., PCT appl. WO 89/06700 (priority: U.S. patent application Ser. No. 146,462, filed Jan. 21, 1988)), and "race" (Frohman, M. A., In: PCR Protocols: A Guide to Methods and Applications, Academic Press, N.Y. (1990)) and "one-sided PCR" (Ohara, O. et al., *Proc. Natl. Acad. Sci.* (*U.S.A.*) 86:5673–5677 (1989)).

Methods based on ligation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)).

An isothermal amplification method has been described in which restriction endonucleases and ligases are used to achieve the amplification of target molecules that contain nucleotide 5'-[α-thio]triphosphates in one strand of a restriction site (Walker, G. T. et al., *Proc. Natl. Acad, Sci.* (*U.S.A.*) 89:392–396 (1992)).

All of the above amplification procedures depend on the principle that an end-product of a cycle is functionally identical to a starting material. Thus, by repeating cycles, the nucleic acid is amplified exponentially.

Methods that use thermocycling, e.g. PCR or Wu, D. Y. et al., *Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

SUMMARY OF THE INVENTION

The present invention concerns a method for achieving the amplification of a nucleic acid molecule using a single primer, under isothermal conditions. In detail, the invention provides a method for amplifying a desired sequence of a target nucleic acid molecule, the sequence having a 3' region, comprising the steps of:

A) incubating the target molecule in the presence of a primer nucleic acid molecule, the molecule being capable of hybridizing to the 3' region of the desired sequence, to thereby form a primer extension product that has a 3' terminus;

B) adapting the 3' terminus of the primer extension product to contain an inverted repeated sequence, the sequence being sufficient to permit a nucleic acid molecule having a recessed 3' terminus to form from the inter-strand hybridization of the inverted repeated sequences;

C) incubating the nucleic acid molecule of step B under conditions sufficient to permit the template dependent extension of the 3' terminus, to thereby form a double-stranded molecule having at least one 3' terminus and one 5' terminus;

D) adapting at least one of the 3' terminus and at least one of the 5' terminus to contain a recombinational site;

E) incubating the adapted double-stranded molecule in the presence of a recombinase under conditions sufficient to form an amplifiable circular molecule containing the desired sequence; and F) incubating the amplifiable circular molecule in the presence of a primer under conditions sufficient to permit the template dependent extension of a primer, the extension thereby amplifying the desired sequence.

The invention particularly concerns the embodiment of the above method wherein at least two double-stranded adapted molecules are formed, or wherein the recombinational site is a loxP site and the recombinase is Cre.

The invention further concerns the embodiments of the above method (1) wherein in step B, the inverted repeated sequence is a recombinational site, (2) wherein in step B, the 3' terminus is adapted by hybridizing the primer extension product to a nucleic acid 3' adaptor molecule having a sequence that is complementary to the sequence of the 3' terminus, and containing inverted repeated sequences, separated by a spacer sequence, or (3) wherein in step B, the 3' terminus is adapted by ligating the primer extension product to a nucleic acid 3' adaptor molecule having a sequence that contains the inverted repeated sequences, separated by a spacer sequence. The spacer sequence may contain a primer binding site which may contain inverted repeated sequences, such that the adaptor molecule contains external inverted repeated sequences, separated by a spacer sequence that contains internal inverted repeated sequences.

The invention also includes the embodiments of the above methods wherein two nucleic acid adaptor molecules are employed, the molecules having the same internal inverted repeated sequences, and a different external inverted repeated sequence.

The invention also includes the embodiments of the above methods wherein the adaptor molecule is at least partially RNA, or is at least partially biotinylated. The invention also includes the embodiments of the above methods wherein the adaptor molecule is single-stranded, or wherein the adaptor molecule is partially single-stranded and partially double-stranded.

The invention particularly concerns the embodiments of the above methods wherein the double-stranded molecule formed in step C has a single 3' terminus and a single 5' terminus, and wherein step D is performed either by adapting the 5' terminus of the primer to contain a sequence, which, in double-stranded form comprises the recombinational site, and forming the recombinational site by template-dependent extension, or by ligating a double-stranded sequence comprising the recombinational site to a and a 5' terminus of the double-stranded nucleic acid molecule of step C.

The invention also provides a double stranded nucleic acid molecule comprising a single 3' and a single 5' terminus, a desired sequence, a sequence complementary to the desired sequence, and a recombinational site.

The invention also provides a kit, being specially adapted to contain in close compartmentalization:

a first container which contains either
  i) a nucleic acid molecule comprising a single-stranded sequence which in double-stranded form would comprise a recombinational site, or
  ii) a nucleic acid molecule whose sequence comprises a recombinational site;
and a second container which contains either
  i) a partially single-stranded, partially double-stranded nucleic acid molecule, or
  ii) a single-stranded nucleic acid molecule, the molecule being capable of adapting the 3' terminus of a desired molecule to contain an inverted repeated sequence;
and optionally, a third containing a recombinase suitable for catalyzing the recombination of the recombinational site sequence of the first container.

BRIEF DESCRIPTION OF THE FIGURES

FIG. 8 shows the amplification replicons of the present invention.

DETAILED DESCRIPTION OF THE INVENTION

I. TERMINOLOGY OF THE INVENTION

Figure 1:
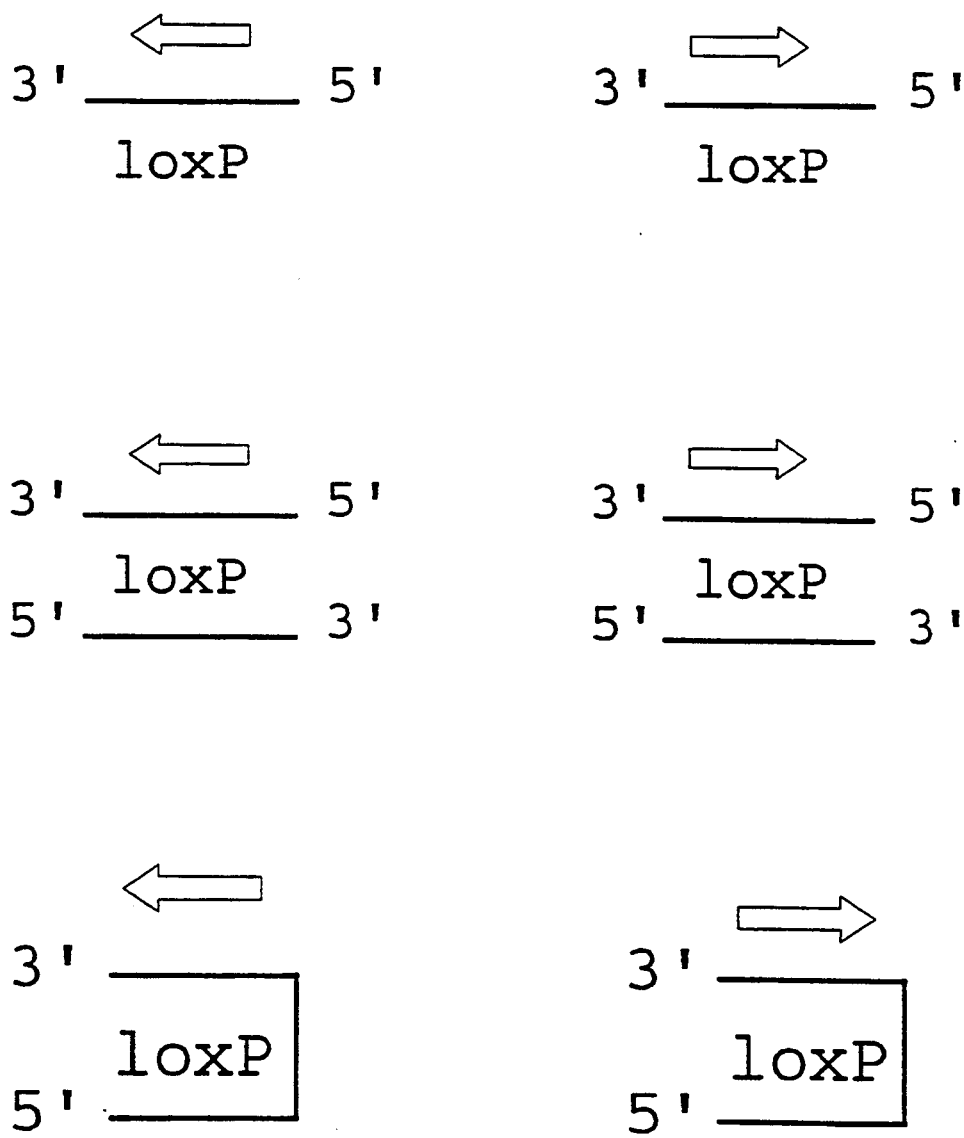
FIG. 1 shows examples of suitable 5' adaptor molecules.

The present invention provides a method for amplifying a "desired" nucleic acid molecule that is present in a sample. Such samples may include biological samples derived from a human or other animal source (such as, for example, blood, stool, sputum, mucus, serum, urine, saliva, teardrop, a biopsy sample, an histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

As used herein, the term "desired nucleic acid molecule" is intended to refer to the nucleic acid molecule that is to be amplified by the present methods. The "desired" molecule can have been purified, or partially purified, or may be present in an unpurified state in the sample. A nucleic acid molecule that contains the "desired" molecule is said to be a "target" molecule.

As used herein, the term "amplification" refers to a "template-dependent process" that results in an increase in the concentration of a nucleic acid molecule relative to its initial concentration. As used herein, the term "template-dependent process" is intended to refer to a process that involves the template-dependent extension of a primer molecule. As such, the term amplification, as used herein, is intended to exclude vector-mediated propagation of the type described by Cohen et al. (U.S. Pat. No. 4,237,224); Maniatis, T. et al., (*Molecular Cloning A Laboratory Manual,* Cold Spring Harbor Laboratory, 1982), etc. The term "template dependent process" refers to nucleic acid synthesis of RNA or DNA wherein the sequence of the newly synthesized strand of nucleic acid is dictated by the well-known rules of complementary base pairing (see, for example, Watson, J. D. et al., *In: Molecular Biology of the Gene,* 4th Ed., W. A. Benjamin, Inc., Menlo Park, Calif. (1987)). As used herein, a sequence of one nucleic acid molecule is said to be the "complement" of another if it contains a T (or U), A, C, or G at a position in which the other molecule contains an A, T (or U), G or C, respectively.

The present invention employs a variety of different enzymes to accomplish the amplification of the desired nucleic acid molecule. A "polymerase" is an enzyme that is capable of incorporating nucleoside triphosphates to extend a 3' hydroxyl terminus of a "primer molecule." As used herein, a "primer" or "primer molecule" is a nucleic acid molecule, that when hybridized to a nucleic acid molecule, possesses a 3' hydroxyl terminus that can be extended by a polymerase. Polymerase enzymes are discussed in Watson, J. D. et al., *In: Molecular Biology of the Gene,* 4th Ed., W. A. Benjamin, Inc., Menlo Park, Calif. (1987), which reference is incorporated herein by reference, and similar texts. Examples of DNA polymerases that can be used in accordance with the methods described herein include *E. coli* DNA polymerase I, the large proteolytic fragment of *E. coli* DNA polymerase I, commonly known as "Klenow" polymerase, "Taq" polymerase, T7 polymerase, T4 polymerase, T5 polymerase, reverse transcriptase, etc.

Polymerases exhibiting processivity (the capacity to continue the extension of a particular primer to thereby produce an extension product of significant length) are preferred.

In several of the embodiments of the present invention, amplification is achieved by extending a hybridized primer on a single-stranded DNA template that is base paired to itself. Thus, polymerases capable of mediating such primer extension are particularly preferred. Examples of preferred polymerases thus include T5 DNA polymerase (Chatterjee, D. K. et al., *Gene* 97:13–19 (1991), T4 polymerase, and T7 polymerase. Where a DNA polymerase does not displace a base-paired stand of a DNA molecule and extend a primer into the previously base-paired region with sufficient efficiency, such capacity may be facilitated by the addition of an accessory protein. For example, the capacity of T7 polymerase to displace a strand of a base-paired molecule is enhanced by the presence of T7 gene 4 protein (Kolodner, R. et al., *J. Biol. Chem* 253:574–584 (1978)). Similarly, T4 DNA polymerase can catalyze extensive primer extension if the reaction additionally contains T4 gene 32 protein (Gillin, F. D. et al., *J. Biol. Chem* 251:5219–5224 (1976)). Use of the T7 promoter and gene 4 protein, however, has the advantage that the gene 4 protein is used catalytically rather than stoichiometrically during the primer extension.

In some embodiments of the invention, amplification is achieved by extending a hybridized primer on a DNA template of a double-stranded DNA molecule composed of two separable strands. Thus, in such embodiments, polymerases capable of mediating such primer extension are preferred. Examples of preferred polymerases thus include the polymerases cited above. The capacity to extend primer molecules using such double-stranded DNA templates may be facilitated through the addition of topisomerases and/or gyrases (Eki, T. et al., *J. Biol. Chem* 266:3087–3100 (1991); Parada, C. A. et al., *J. Biol. Chem* 264:15120–15129 (1989)).

When an enzymatic reaction, such as a polymerization reaction, is being conducted, it is preferable to provide the components required for such reaction in "excess" in the reaction vessel. "Excess" in reference to components of the amplification reaction refers to an amount of each component such that the ability to achieve the desired amplification is not substantially limited by the concentration of that component.

A "ligase" is an enzyme that is capable of covalently linking the 3' hydroxyl group of a nucleotide to the 5' phosphate group of a second nucleotide. Ligases capable of joining "blunt ended" or "staggered ended" double-stranded nucleic acids, may be employed. Examples of suitable ligases include *E. coli* DNA ligase, T4 DNA ligase, etc.

The present invention employs a "recombinase," and most preferably, a "site-specific recombinase." As used herein, a recombinase is an enzyme whose action on two nucleic acid molecules results in recombination between the two molecules. Recombination is a well-studied natural process which results in the scission of two nucleic acid molecules having identical or substantially similar sequences (i.e. "homologous"), and the ligation of the two molecules such that one region of each initially present molecule becomes ligated to a region of the other initially present molecule (Sedivy, J. M., *BiO-Technol.* 6:1192–1196 (1988), which reference is incorporated herein by reference). Recombinases are naturally present in both prokaryotic and eucaryotic cells (Smith, G. R., In: *Lambda II,* (Hendrix, R. et al., Eds.), Cold Spring Harbor Press, Cold Spring Harbor, N.Y., pp. 175–209 (1983), herein incorporated by reference)).

Two types of recombinational reactions have been identified. In the first type of reaction, "general" or "homologous" recombination, any two homologous sequences can be recognized by the recombinase (i.e. a "general recombinase"), and can thus act as substrates for the reaction. In contrast, in the second type of recombination, termed "site-specific" recombination, the recombinase can catalyze recombination only between certain specialized "recombinational sites." Thus, in "site-specific recombination," only homologous molecules having a particular sequence may act as substrates for the reaction.

Site specific recombination is thus mediated by a site-specific recombinase acting on two "recombinational sites." Several such site-specific recombination systems have been described. The most preferred site specific recombinational system is the site-specific recombination system of the *E. coli* bacteriophage P1. The P1 bacteriophage cycles between a quiescent, lysogenic state and an active, lytic state. The bacteriophage's site-specific recombination system catalyzes the circularization of P1 DNA upon its entry into a host cell. It is also involved in the breakdown of dimeric P1 DNA molecules which may form as a result of replication or homologous recombination.

The P1 site-specific recombination system catalyzes recombination between specialized sequences, known as "loxP" sequences. The loxp site has been shown to consist of a double-stranded 34 bp sequence. This sequence contains two 13 bp inverted repeated sequences which are separated from one another by an 8 bp spacer region (Hoess, R. et al., *Proc. Natl. Acad. Sci. (U.S.A.)* 79:3398-3402 (1982); Sauer, B. L., U.S. Pat. No. 4,959,317, herein incorporated by reference).

The recombination is mediated by a P1-encoded protein known as "Cre" (Hamilton, D. L. et al., *J. Molec. Biol.* 178:481-486 (1984), herein incorporated by reference). The Cre protein mediates recombination between two loxP sequences (Sternberg, N. et al., *Cold Spring Harbor Symp. Quant. Biol.* 45:297-309 (1981)). These sequences may be present on the same DNA molecule, or they may be present on different molecules. Cre protein has a molecular weight of 35,000. The protein has been purified to homogeneity, and its reaction with the loxP site has been extensively characterized (Abremski, K. et al., *J. Molec. Biol.* 259:1509-1514 (1984), herein incorporated by reference). The cre gene (which encodes the Cre protein) has been cloned (Abremski, K. et al., *Cell* 32:1301-1311 (1983), herein incorporated by reference). Cre protein can be obtained commercially from New England Nuclear/Dupont.

The site specific recombination catalyzed by the action of Cre protein on two loxP sites is dependent only upon the presence of the above-described thirty-four base pair long loxP site and Cre. No energy is needed for this reaction; thus, there is no requirement for ATP or other similar high energy molecules. Moreover, no factors or proteins other than the Cre protein is required in order to mediate site specific recombination at loxP sites (Abremski, K. et al., *J. Molec. Biol. Chem.* 259:1509-1514 (1984)). In vitro, the reaction is highly efficient; Cre is able to convert 70% of the DNA substrate into products and it appears to act in a stoichiometric manner (Abremski, K. et al., *J. Molec. Biol. Chem.* 259:1509-1514 (1984)).

Cre-mediated recombination can occur between loxP sites which are present on two different molecules. Because the internal spacer sequence of the loxP site is asymmetrical, two loxP sites exhibit directionality relative to one another (Hoess, R. H. et al., *Proc. Natl. Acad. Sci. (U.S.A.)* 81:1026-1029 (1984)). If the loxP sites are in the same relative orientation, Cre acts to excise and circularize the DNA between them. If the sites are in an opposite relative orientation, cre acts to flip the DNA between them. The recombinational event works efficiently on linear or circular molecules (Abremski, K. et al., *Cell* 32:1301-1311 (1983); Abremski, K. et al., *J. Molec. Biol. Chem.* 261:391-396 (1986)).

The nature of the interaction between Cre and a loxP site has been extensively studied (Hoess, R. P. et al., *Cold Spring. Harb. Symp. Quant. Biol.* 49:761-768 (1984), herein incorporated by reference). In particular, mutations have been produced both in Cre, and in the loxP site.

The Cre mutants thus far identified have been found to catalyze recombination at a much slower rate than that of the wild-type Cre protein. loxP mutants have been identified which recombine at lower efficiency than the wild-type site (Abremski, K. et al., *J. Molec. Biol. Chem.* 261:391-396 (1986); Abremski, K. et al., *J. Molec. Biol.* 202:59-66 (1988), herein incorporated by reference).

Experiments with mutant loxP sites in which either the left or right inverted repeat had been removed, has revealed that Cre is capable of binding to partial loxP sites, but is incapable of mediating efficient recombination between such sites. Insertions in the spacer region impair the ability of Cre to catalyze recombination. Of particular interest to the present invention is the use of a loxP511 mutant site.

The Cre protein is capable of mediating loxP-specific recombination in eucaryotic hosts, such as *Saccharomyces cerevisiae* (Sauer, B., *Molec. Cell. Biol.* 7:2087-2096 (1987); Sauer. B. L., U.S. Pat. No. 4,959,317, herein incorporated by reference), or mammalian cells (Sauer, B. et al., *Proc. Natl. Acad. Sci. (U.S.A.)* 85:5166-5170 (1988), Sauer, B. et al., *Nucleic Acids Res.* 17:147-161 (1989), both references herein incorporated by reference).

Significantly, the loxP-Cre system can mediate site-specific recombination between loxP sites separated by extremely large numbers of nucleotides (Sauer, B. et al., *Gene* 70:331-341 (1988); Sternberg, N., *Proc. Natl. Acad. Sci. (U.S.A.)* 87:103-107 (1990); Sauer, B. et al., *Proc. Natl. Acad. Sci. (U.S.A.)* 84:9108-9112 (1987); Palazzolo, M. J. et al., *Gene* 88:25-36 (1990), all herein incorporated by reference).

It has been found that certain *E. coli* enzymes inhibit efficient circularization of linear molecules which contain two loxP sites. Hence, enhanced circularization efficiency can be obtained through the use of *E. coli* mutants which lack exonuclease V activity (Sauer, B. et al., *Gene* 70:331-341 (1988)).

Although the Cre-loxP site-specific recombination system is preferred, alternative site-specific recombination systems have been identified, and can be used in accordance with the methods of the present invention.

For example, the site-specific recombination system of the *E. coli* bacteriophage λ (Weisberg, R. et al., In: *Lambda II*, (Hendrix, R. et al., Eds.), Cold Spring Harbor Press, Cold Spring Harbor, N.Y., pp. 211-250 (1983), herein incorporated by reference) can be employed. Bacteriophage λ uses this recombinational system in order to integrate its genome into its host, the bacterium *E. coli*. The system is also employed to excise the bacteriophage from the host genome in preparation for virus' lytic growth.

The λ recombination system is composed of four proteins—Int and Xis, which are encoded by the virus, and two host factors encoded by the *E. coli*. These proteins catalyze site-specific recombination between "att" sites.

The λ Int protein (together with the *E. coli* host integration factors) will catalyze recombination between "attP" and "attB" sites. If the attP sequence is present on a circular molecule, and the attB site is present on a linear molecule, the result of the recombination is the disruption of both att sites, and the insertion of the entire attP-containing molecule into the attB site of the second molecule. The newly formed linear molecule will contain an attL and an attR site at the termini of the inserted molecule.

The λ Int enzyme is unable to catalyze the excision of the inserted molecule. Thus, the reaction is unidirectional. In the presence of the λ Xis protein, the reverse reaction can proceed, and a site-specific recombinational event will occur between the attR and attL sites to regenerate the initial molecules.

The nucleotide sequence of both the Int and Xis proteins are known, and both proteins have been purified to homogeneity. Both the integration and the excision reaction can be conducted in vitro. The nucleotide sequences of the four att sites has also been determined (Weisberg, R. et al., In: *Lambda II*, (Hendrix, R. et al., Eds.), Cold Spring Harbor Press, Cold Spring Harbor, N.Y., pp. 211–250 (1983), which reference has been herein incorporated by reference).

Additional site-specific recombination systems that may be employed include TpnI and the β-lactamase transposons (Levesque, R. C., *J. Bacteriol.* 172:3745–3757 (1990)); the Tn3 resolvase (Flanagan, P. M. et al., *J. Molec. Biol.* 206:295–304 (1989); Stark, W. M. et al., *Cell* 58:779–790 (1989)); the yeast recombinases (Matsuzaki, H. et al., *J. Bacteriol.* 172:610–618 (1990)); the *B. subtilis* SpoIVC recombinase (Sato, T. et al., *J. Bacteriol.* 172:1092–1098 (1990)); the Flp recombinase (Schwartz, C. J. et al., *J. Molec. Biol.* 205:647–658 (1989); Parsons, R. L. et al., *J. Biol. Chem.* 265:4527–4533 (1990); Golic, K. G. et al., *Cell* 59:499–509 (1989); Amin, A. A. et al., *J. Molec. Biol.* 214:55–72 (1990)); the Hin recombinase (Glasgow, A. C. et al., *J. Biol. Chem.* 264:10072–10082 (1989)); immunoglobulin recombinases (Malynn, B. A. et al., *Cell* 54:453–460 (1988)); and the Cin recombinase (Hafter, P. et al., *EMBO J.* 7:3991–3996 (1988); Hubner, P. et al., *J. Molec. Biol.* 205:493–500 (1989)), all herein incorporated by reference. Such alternate systems are discussed by Echols, H. (*J. Biol. Chem.* 265:14697–14700 (1990)), de Villartay, J. P. (*Nature* 335:170–174 (1988); Craig, N. L. (*Ann. Rev. Genet.* 22:77–105 (1988)), Poyart-Salmeron, C. et al. (*EMBO J.* 8:2425–2433 (1989)), Hunger-Bertling, K. et al. (*Molec. Cell. Biochem.* 92:107–116 (1990)), and Cregg, J. M. (*Molec. Gen. Genet.* 219:320–323 (1989)), all herein incorporated by reference.

Conditions or agents which increase the rate or the extent of priming, primer elongation, or strand displacement, may be used to increase the extent of the amplification obtained with the methods of the present invention. For instance, as indicated above, the addition of topoisomerases, helicases, gyrases or single-stranded nucleic acid binding proteins (such as the gene 32 protein of T4 or the gene 4 protein of T7) may be used to increase the strand displacement rate of a DNA polymerase, or may allow the use of a DNA polymerase that might not ordinarily give substantial amplification.

It is desirable to provide to the assay mixture an amount of required co-factors such as $Mg^{++}$, and dATP, dCTP, dGTP, dTTP, ATP, CTP, GTP, UTP or other nucleoside triphosphates in sufficient quantity to support the degree of amplification desired. Nucleoside triphosphate analogues, etc. (Piccirilli, J. A. et al., *Nature* 343:33–37 (1990) can be substituted or added to those specified above, provided that the base pairing, polymerase and strand displacing functions are not adversely affected to the point that the amplification does not proceed to the desired extent.

II. THE MOLECULES EMPLOYED IN THE AMPLIFICATION METHOD

A. The Nature of the Desired Molecule

The methods of the present invention may be used to amplify any desired nucleic acid molecule. Such molecules may be either DNA or RNA. The molecule may be homologous to other nucleic acid molecules present in the sample (for example, it may be a fragment of a human chromosome isolated from a human cell biopsy, etc.). Alternatively, the molecule may be heterologous to other nucleic acid molecules present in the sample (for example, it may be a viral, bacterial, or fungal nucleic acid molecule isolated from a sample of human blood, stools, etc.). The methods of the invention are capable of simultaneously amplifying both heterologous and homologous molecules. For example, amplification of a human tissue sample infected with a virus may result in amplification of both viral and human sequences.

The present methods do not require that the desired molecule have any particular sequence or length. In particular, the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Mycoplasma, etc.), eucaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the desired nucleic acid sequence may or may not be found in nature.

The desired nucleic acid molecule which is to be amplified may be in either a double-stranded or single-stranded form. However, if the nucleic acid is double-stranded at the start of the amplification reaction it is preferably first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)), which references are herein incorporated by reference.

Macromolecular entities that contain nucleic acid other than double-stranded DNA, or single-stranded DNA, such as single-stranded RNA, double-stranded RNA or mRNA are capable of being amplified by the method of the invention. For example, the RNA genomes of certain viruses can be converted to DNA by reaction with enzymes such as reverse transcriptase (Maniatis, T. et al., *Molecular Cloning (A Laboratory Manual)*, Cold Spring Harbor Laboratory, 1982; Noonan, K. F. et al., *Nucleic Acids Res.* 16:10366 (1988)). The product of the reverse transcriptase reaction may then be amplified according to the invention.

The complete nucleotide sequence of the desired molecule need not be known in order to employ the methods of the present invention. The present invention, like PCR, requires knowledge only of the sequences that flank the sequence that is to be amplified. The desired sequence may thus be envisioned as consisting of three regions. The first region, corresponding to the 3' terminus of the desired molecule that is to be amplified is the region to which the single-primer of the present invention hybridizes. Thus, the sequence of this first region must be ascertained in order to construct a complementary primer that would be capable of hybridizing to the desired molecule.

As used herein, two sequences are said to be able to hybridize to one another if they are complementary and are thus capable of forming a stable anti-parallel double-stranded nucleic acid structure. Conditions of nucleic acid hybridization suitable for forming such double stranded structures are described by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)).

For the purpose of hybridizing the primer to the first region of the desired molecule, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

The size of the first region of the desired molecule is such as to permit the primer molecule to stably hybridize to it. Preferably, therefore, the first region of the desired molecule will be greater than 10 nucleotides in length, and most preferably, 15 to 50 nucleotides in length. Longer or shorter primers may be used, however. The use of shorter primers may result in the amplification of nucleic acid sequences in addition to that of the desired sequence. The use of longer primers may slow the rate of hybridization. Extension of the primer may be done with reverse transcriptase where the desired molecule is present as RNA. Alternatively, such extension can be accomplished with other DNA polymerases where the desired molecule is DNA.

The second region of the desired molecule is located 5' to the first region, and consists of the central portion of the desired molecule. The second region of the desired molecule may have any sequence, and be of any length. As stated above, the sequence of this region need not be known in order to follow the methods of the present invention. Typically, the second region may extend from a few nucleotides to several kilobases.

The third region of the desired molecule is located at the 5' terminus of the desired molecule. The sequence of this region must be known in order to follow the methods of the present invention. Typically, the third region may extend from as few as 3 nucleotides to 10–20. If the third region is not used as a template for a primer, it need not be of a length sufficient to permit stable priming. In a preferred embodiment, however, the third region must be of sufficient length to permit stable hybridization to occur. In this embodiment, the third region is preferably of a length of 15 to 50 nucleotides in length. Longer or shorter primers may be used, however.

Thus, the extent of sequence information of the desired molecule that is needed to practice the present invention is typically less than that needed to practice PCR methods.

B. The Nature of the Single Primer

The present invention employs a single primer to achieve the amplification of the desired molecule. The primer molecule that is used in the present amplification method is of suitable length to stably hybridize to the first region of the desired molecule. Primer molecules of 10–50 nucleotides are thus suitable.

Any of a variety of methods can be used to produce the primer molecule. For example, the molecule can be excised from a vector that contains it using suitable enzymes, such as restriction enzymes. Most preferably, however, the primer will be made synthetically, using well-known chemical methods.

C. The Adaptor Molecules of the Invention

The present invention employs specialized "adaptor molecules" to alter the 5' terminus of the primer or primer extension product that is formed from the template dependent extension of the above-described primer molecule, and the 3' terminus of the primer extension product. The adaptor molecules may be either a partially single-stranded, partially double-stranded nucleic acid molecule, or it may be a single-stranded molecule. Thus, in one embodiment, the adaptation of the 5' terminus is accomplished by employing a primer molecule whose 5' terminus is designed such that it contains the desired adaptation. In a second embodiment, the 5' terminus of the primer extension product is altered using a 5' adaptor molecule. With respect to the alteration of the 3' terminus of the primer extension product, such alteration can be accomplished using either a single adaptor molecule, or, in an alternate embodiment with a pair of adaptor molecules having similar structure (and resulting in a mixture of primer extension products, some of which have been modified by one of the 3' adaptor molecules, and some of which have been modified by the other 3' adaptor molecule).

The adaptor molecules permit the linear primer extension product to form either single-stranded or double-stranded circular nucleic acid molecules which may be readily amplified under isothermal conditions.

1) The Adaptor Molecules of the 5' Terminus

An adaptor molecule is used to modify the 5' terminus of the primer molecule or the primer extension product such that it contains a recombinational site, most preferably a loxP site.

The adaptor molecule of the 5' terminus can be added to the primer molecule either before or after its template dependent extension. In the most preferred embodiment, the primer molecule is modified to contain the 5' adaptor molecule prior to extension. Thus, in this embodiment, the primer may be synthesized such that it contains an additional region (including the recombinational site) at its 5' terminus. In this embodiment, when employing a recombinational site that, like loxP exhibits directionality, it is generally necessary that some of the primer must be synthesized with the loxP site in one orientation, and some of the primer must be synthesized with the loxP site in the opposite orientation. Molecules having only a single orientation can be used in conjunction with a 3' adaptor molecule that contains a recombinational site of an opposing orientation.

Alternatively, however, the 5' terminus can be modified through the action of a ligase using either single-stranded or, more preferably, double-stranded DNA containing the recombinational site. In one embodiment, such ligation substrates will possess a 5' terminus (such as a 5' hydroxyl group) that prevents the ligation of more than one such ligation substrate molecule to the primer extension molecule. Alternatively, the adaptor molecule may be a single-stranded molecule, that exhibits intra-strand hybridization (i.e. a "hairpin" loop). As in the case of the adapted primer molecule discussed above, the use of a recombinational site having directionality will generally require the use of two hairpin loop species having opposite orientations for their recombinational sites. Additional sequences may, if desired, be added 3' or 5' of the recombinational site. Examples of suitable 5' adaptor molecules are shown in FIG. 1.

2) The Adaptor Molecules of the 3' Terminus

Any of a variety of different adaptor molecules can be used to alter the 3' terminus of the primer extension molecule. The choice of which type of adaptor molecule to use will depend upon whether the formation of single-stranded or double-stranded molecules is preferred. Examples of suitable 3' adaptor molecules are shown in FIG. 2.

a) Adaptor Molecules for the Formation of Single-Stranded Circular Molecules: Use of Partially Single-Stranded and Partially Double-Stranded 3' Adaptor Molecules In one embodiment, partially single-stranded and partially double-stranded nucleic acid adaptor molecules are employed to alter the 3' terminus of the primer extension product as a prelude to the formation of single-stranded circular molecules. A feature of such molecules is that they possess a 3' protruding region having a predefined sequence. The sequence of this protruding sequence is selected such that 3' -most portion of the region has the same sequence as that of the third region of the desired molecule. In a first preferred sub-embodiment, this protruding terminus is blocked, as by the use or presence of a dideoxynucleotide, etc., such that it is incapable of being extended by a polymerase in a template-directed process.

The strand of the adaptor molecule that contains the 3' protruding sequence may be composed of RNA, such that it can be readily degraded by the inclusion of RNAse to the reaction, or by alkali treatment. Methods of forming RNA oligonucleotides are disclosed by Sharmeen, L. et al. (*Nucleic Acids Res.* 15:6705–6711 (1987)) and by Milligan, J. F., et al., *Nucleic Acids Res.* 15:8783–8798 (1987)). In another embodiment, the strand of the adaptor molecule that contains this protruding sequence is composed of a nucleic acid that has been biotinylated, such that the strand can be selectively removed from the reaction by addition of agents such as anti-biotin antibodies, avidin, streptavidin, etc.

A second feature of the adaptor molecules is the presence of a double-stranded region located 5' to the above-described protruding 3' terminus.

Figure 2A:
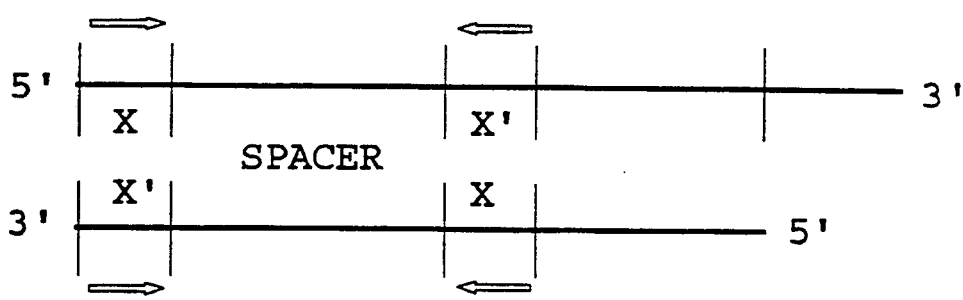
FIG. 2 shows examples of suitable 3' adaptor molecules.
Figure 2A:
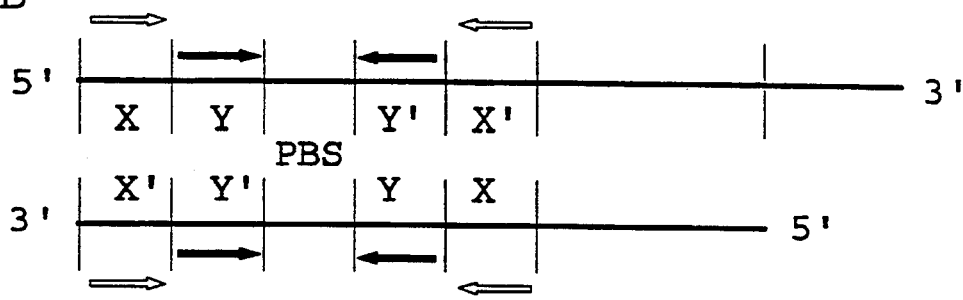
Figure 2A:
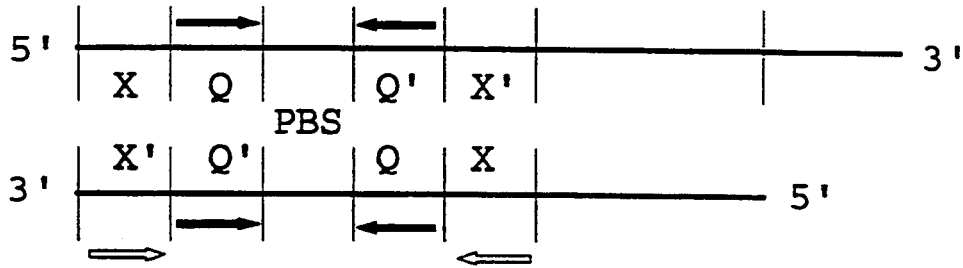

In one embodiment, the invention employs a single such 3' terminus adaptor molecule whose double-stranded region comprises a pair of inverted repeated sequences, preferably separated by a spacer sequence. This aspect of the invention is shown in FIG. 2A, wherein the terms X and X' are used to designate complementary sequences that comprise the inverted repeated sequence. The spacer sequence is preferably 3–100 nucleotides in length. The length of the spacer is selected such that the inverted repeated sequences are sterically capable of hybridizing to one another. Thus, if the inverted repeated sequences are of sufficient length, the sequences will be capable of hybridizing to one another in the absence of a spacer sequence. In a preferred embodiment, however, the spacer sequence is 10–50 nucleotide long, and preferably not an inverted repeated sequence. In this embodiment, the spacer sequence is adapted to function as a primer binding site (designated "PBS" in the Figures) for the amplification of the desired sequence.

Figure 2B:
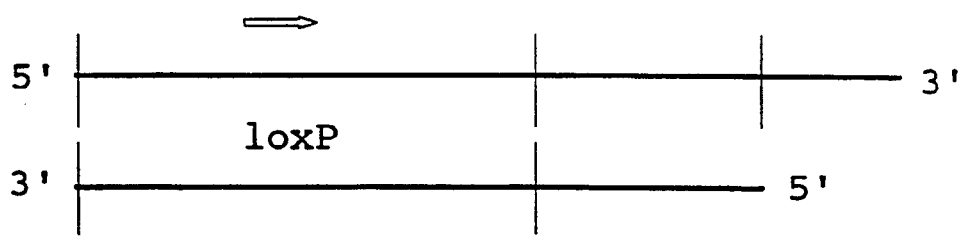
Figure 2B:
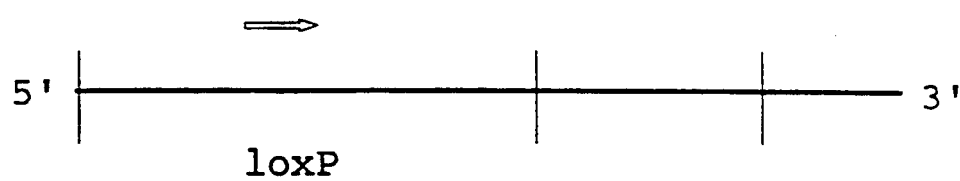
Figure 2B:
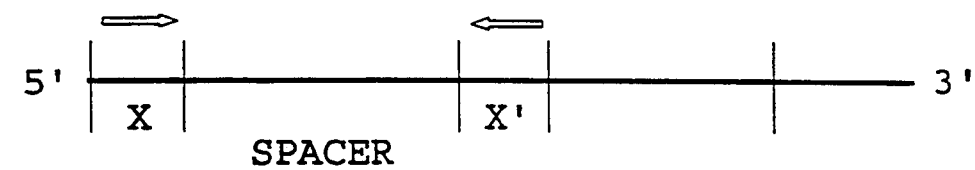
Figure 2B:
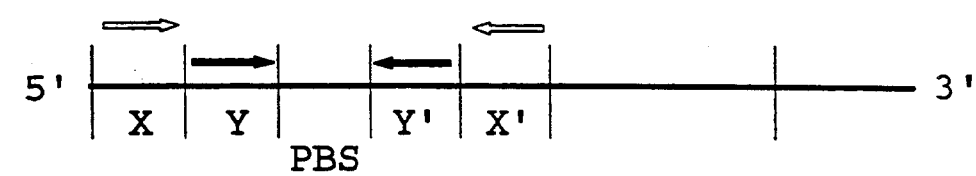
Figure 2B:
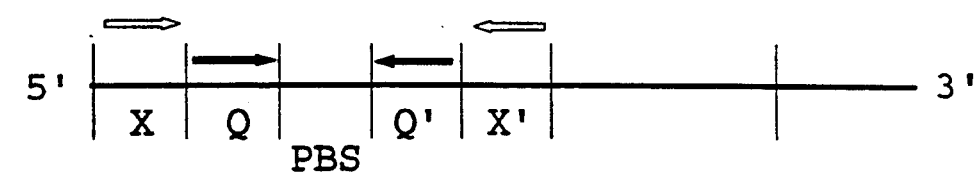

In an alternate preferred embodiment, the invention employs two different 3' terminus adaptor molecules. In each of these adaptor molecules, the spacer sequence is composed of a second pair of inverted repeated sequences, such that the structure of the adaptor molecule provides a pair of external inverted repeated sequences that flank a pair of internal inverted repeated sequences. In a preferred embodiment, the sequences of the pair of internal inverted repeated sequences are interrupted by a primer binding site that is preferably 10–50 bases long, and preferably not an inverted repeated sequence. This aspect of the invention is shown in FIG. 2B, where the term "PBS" is used to designate the relative position of the optional primer binding site, the terms Y and Y' or Q and Q' are used to designate complementary sequences that comprise the optional internal inverted repeated sequences, and the terms X and X' are used to designate complementary sequences that comprise the external inverted repeated sequences. In the most preferred sub-embodiment of this embodiment, the sequences of the external and internal repeated sequences are different. The sequences of the two adaptor molecules are selected such that the nucleotide sequence of the external inverted repeat sequence of the first of the two adaptor molecules is different from the external inverted repeated sequence of the second of the two adaptor molecules. The sequences of the external inverted repeats of the first and second adaptor molecules are thus selected such that they are substantially incapable of hybridizing to one another (i.e. the external repeat sequence of the first adaptor molecule is substantially incapable of hybridizing to the external inverted repeat of the second adaptor molecule). The nucleotide sequence of the internal inverted repeated sequences of the two adaptor molecules is preferably the same, or at least sufficiently similar to allow the respective internal repeated sequences of the adaptor molecules to hybridize to one another. If the internal repeated sequences are interrupted by a primer binding site, such sequences may be different, but will preferably be the same.

As used herein, two sequences are said to be "inverted repeats" of one another if they are complementary to one another. Thus, a feature of the adaptor molecules is that, although the inverted repeat sequences of the two strands of the double-stranded region of the adaptor molecules are hybridized to one another in the adaptor molecule, they would be capable of intra-strand hybridization (i.e. "snapping-back" and forming a hairpin loop structure) if the adaptor molecule were denatured or converted to a single-stranded form. The length of the inverted repeated sequences is selected such that intra-strand hybridization would be possible if the adaptor molecule were denatured or converted to a single-stranded form. Thus, the inverted repeated sequences are preferably greater than 10 nucleotides in length, and most preferably, 15 to 50 or more nucleotides in length. Longer or shorter inverted repeated sequences may however be used. The use of shorter inverted repeated sequences may result in a decreased rate of hairpin formation. The use of longer sequences may lead to a destablization of inter-strand hybridization, and thus may be undesirable where such hybridization is desired.

When defining conditions to be used in any specific embodiment of the present invention, it is desirable to select a primer that cannot prime on itself. To minimize the likelihood of potential interfering reactions, candidate primers should be tested in reactions which address this issue prior to use in the amplification process. One such example is to measure the addition of nucleotides by a polymerase to the 3' end of the candidate primer in the absence of any target molecule.

The above-described adaptor molecules can be synthesized using any of a variety of methods. For example, the "inverted repeated sequence-inverted repeated sequence," "inverted repeated sequence-spacer sequence-inverted repeated sequence" or the "external inverted repeated sequence-internal inverted repeated sequence-internal inverted repeated sequence-external inverted repeated sequence" segment of the adaptor molecules can be obtained by cloning such a sequence, propagating the vector, and then excising the sequence using a restriction endonuclease. The protruding 3' terminus can be formed using deoxynucleotide terminal transferase and the appropriate nucleotide triphosphates. In following such a method, it would be desirable to block the 3' terminus of the second strand of the adaptor molecule. Alternatively, the protruding 3' terminus can be added by ligating a single- or double-stranded molecule to the "inverted repeat-inverted repeat" segment of the adaptor molecule (or any of the above-described variants thereof), and then removing the sequence complementary to the "protruding 3' sequence" to thereby render that sequence actually protruding.

In a preferred embodiment, the strands of the adaptor molecule(s) are prepared separately (preferably by primer extension using suitable primers and templates, or by clonal propagation, by transcription, by synthetic means, or by any combination of these methods), and then mixed together under conditions sufficient to permit the molecules to hybridize to one another. This method is particularly suited to the embodiments wherein the strand that contains the protruding 3' end is RNA or is biotinylated. Those of ordinary skill will readily comprehend alternative methods for forming the adaptor molecules.

b) Adaptor Molecules for the Formation of Single-Stranded Circular Molecules: Use of Single-Stranded 3' Adaptor Molecules In a second, and preferred, sub-embodiment, the adaptor molecule(s) in the formation of single-stranded circular molecules will be single-stranded DNA (preferably biotinylated) or RNA molecules. Such molecules will have a sequence and structure that are identical to the structure of the that strand of the above-described partially single-stranded and partially double-stranded adaptor molecules which contain the discussed protruding 3' terminus. In the most preferred embodiment, the 3' terminus of the molecule is blocked, such that it cannot be extended by a polymerase.

c) Adaptor Molecules for the Formation of Double-Stranded Circular Molecules

The above-described 3' adaptor molecules are designed to permit the formation of single-stranded circular molecules. In order to form double-stranded circular molecules, a different type of 3' adaptor molecule is preferably employed.

In this embodiment of the invention, the 3' terminus of the primer extension product is modified such that it contains a recombinational site. If a site such as loxP is employed, the orientation of the site must be such that upon adaptation, the two loxP sites are present in a direct repeat orientation. For such purpose, a partially single-stranded and partially double-stranded adaptor molecule or a single-stranded molecule is employed. The partially single-stranded and partially double-stranded adaptor molecule will have a protruding 3' terminus that is capable of hybridizing to the primer extension product in the manner described above, and of being extended in a template-dependent manner. The double-stranded region of the molecule, located 5' to the protruding 3' terminus, will comprise a recombinational site. Most preferably, the double-stranded region will also contain a region that is substantially incapable of participating in inter-strand hybridization flanked by sequences that are capable of participating in such hybridization. Most preferably, such incapacity is obtained through the use of sequences that are identical, and have the attributes of the primer binding sequence discussed above. Such a molecule is illustrated in FIG. 2C. If a single-stranded 3' terminus adaptor molecule is employed, the molecule will preferably contain the same structure and sequence as that strand of the above-described partially single-stranded and partially double-stranded adaptor molecule that possess the protruding 3' terminus.

D. The Amplification Substrates

The present invention employs amplification substrate molecules in order to achieve the amplification of the desired molecule.

The amplification substrates are preferably either the primer molecule used to form the primer extension product (either containing or lacking the 5' recombinational site), or, more preferably, a sequence complementary to that of the optional primer binding site of the 3' terminus adaptor molecule.

III. THE AMPLIFICATION METHODS OF THE PRESENT INVENTION

A. The First Step of the Methods: Primer Extension

In the first step of the amplification methods of the present invention, the nucleic acid molecules of the sample are incubated with the above-described single primer molecule in the presence of DNA polymerase, and requisite nucleotide triphosphates and co-factors. The molecules are incubated under conditions sufficient to permit the primer to hybridize to its target sequence, and to be extended to form a primer extension product. Thus, if the desired sequence is a double-stranded DNA or RNA molecule, the strands are separated as by heat denaturation, or other means. If the desired sequence is a single-stranded DNA or RNA molecule, the denaturation step may be omitted.

In one embodiment of the invention, as for example when the concentration of the desired molecule is anticipated to be low, the molecules can be denatured and renatured in a cyclical manner so as to permit repeated rounds of primer extension. In this embodiment, the use of thermostable polymerases, such as Taq polymerase is preferred, so that the expense of adding new polymerase can be avoided.

Most preferably, the conditions of the primer extension will be controlled such that the average length of the extended primers will be the length separating the beginning of the first region from the end of the third region of the desired molecule. Such controlling of conditions can be accomplished by altering the concentration of DNA polymerase, the duration of the polymerization reaction, or by limiting the concentration of a nucleotide triphosphate such that "stuttering" of the primer extension product occurs when it reaches the desired average length.

After primer extension has been completed, the reaction is treated, preferably with heat or RNAse H (if the target molecule was RNA) so as to denature double-stranded nucleic acid molecules and render such molecules single-stranded. If desired, excess primer can be removed from the sample (as by filtration, adsorption, etc.), however, such action is not necessary to the invention.

B. The Second Step of the Methods: Adaptation of the 3' Terminus of the Primer Extension Product The second step of the method entails the adaptation of the primer extension product such that it is capable of conversion into a circular molecule. The adaptation of the 3' terminus may precede or follow the adaptation of the 5' terminus, depending upon the adaptor molecules selected. Adaptation of the termini may also be accomplished simultaneously. As indicated, the adaptation of the 5' terminus may be accomplished through the use of modified primers, and may thus be accomplished prior to the primer extension step.

1) Further Primer Extension

Figure 3A:
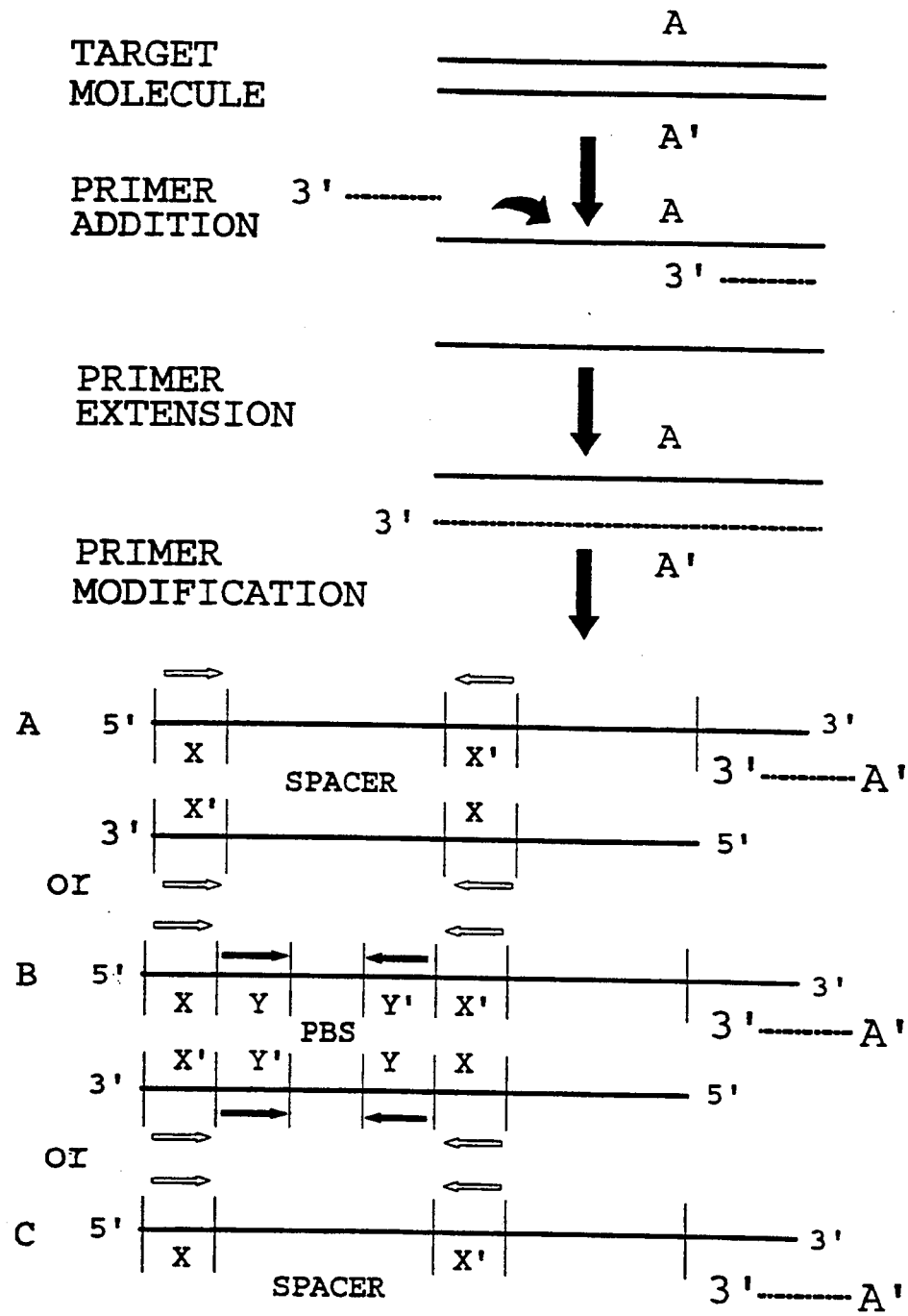
FIG. 3 shows the adaptation of the 3' terminus of the primer extension product. Lines A, B, and C of FIG. 3 illustrate the use of different adaptor molecules to modify the 3' terminus of the primer extension product through further primer extension. Line D of FIG. 3 shows the use of ligation to modify the 3' terminus.
Figure 3B:
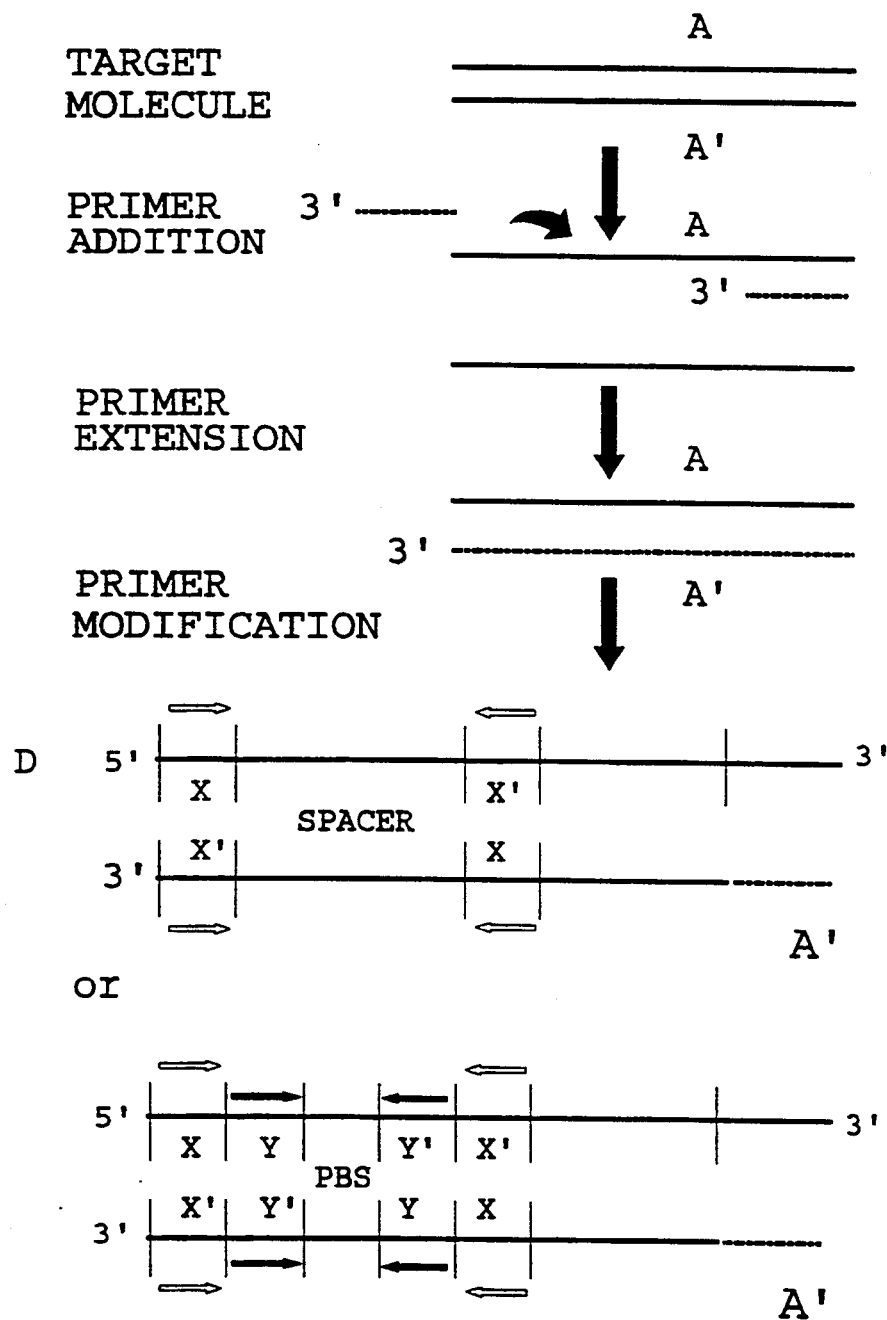
Figure 4A:
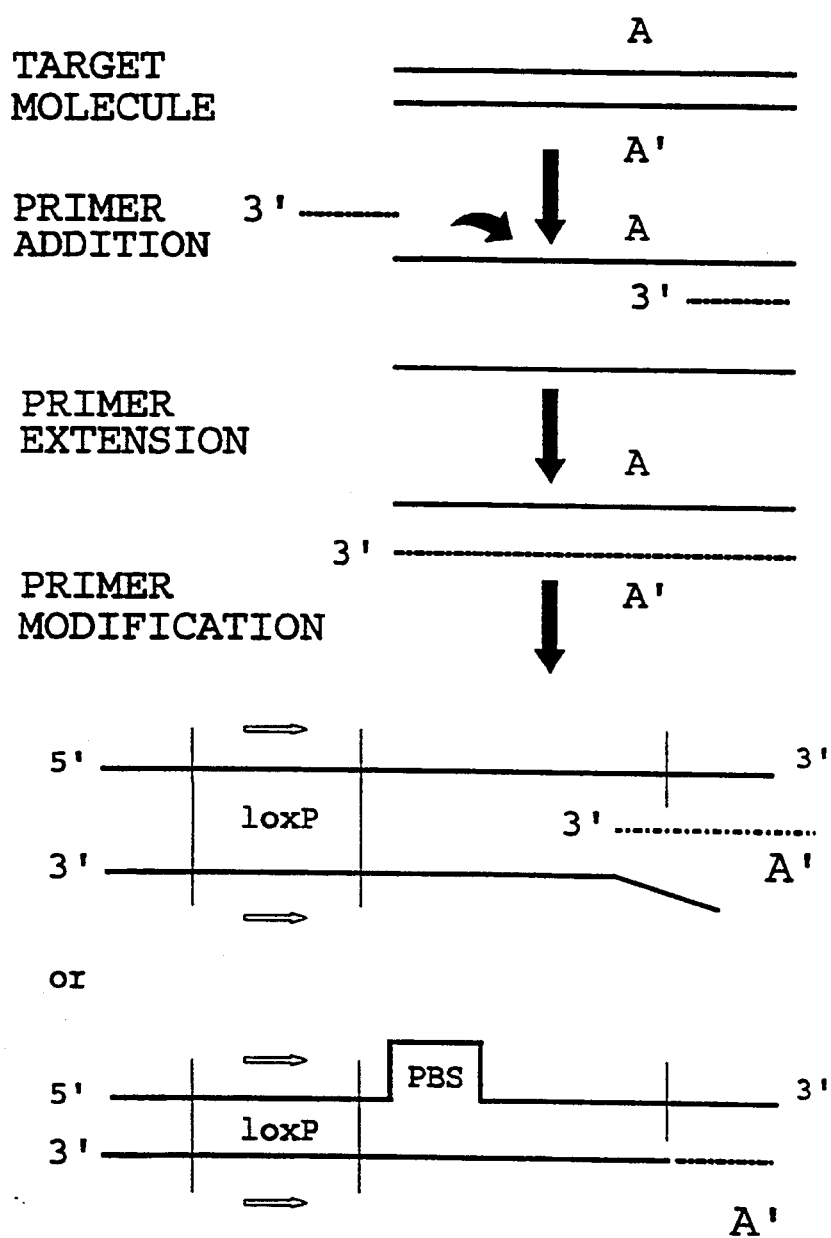
FIG. 4 shows the formation of double-stranded circular molecules from linear molecules adapted using adaptor molecules that contain a recombinational site.
Figure 4B:
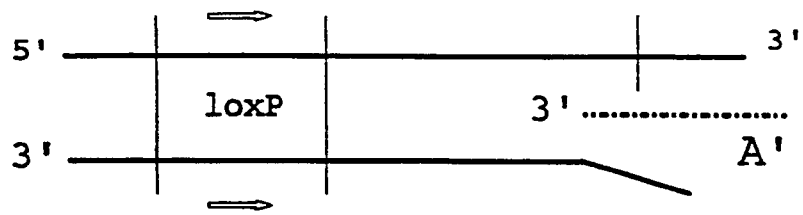
Figure 4B:
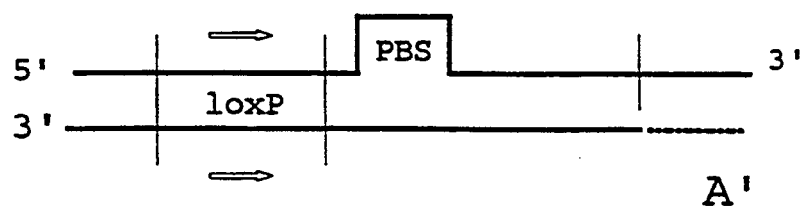
Figure 4B:
Figure 4B:
Figure 4B:
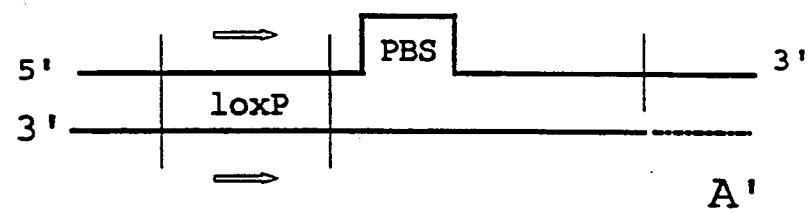
Figure 4B:
Figure 4C:
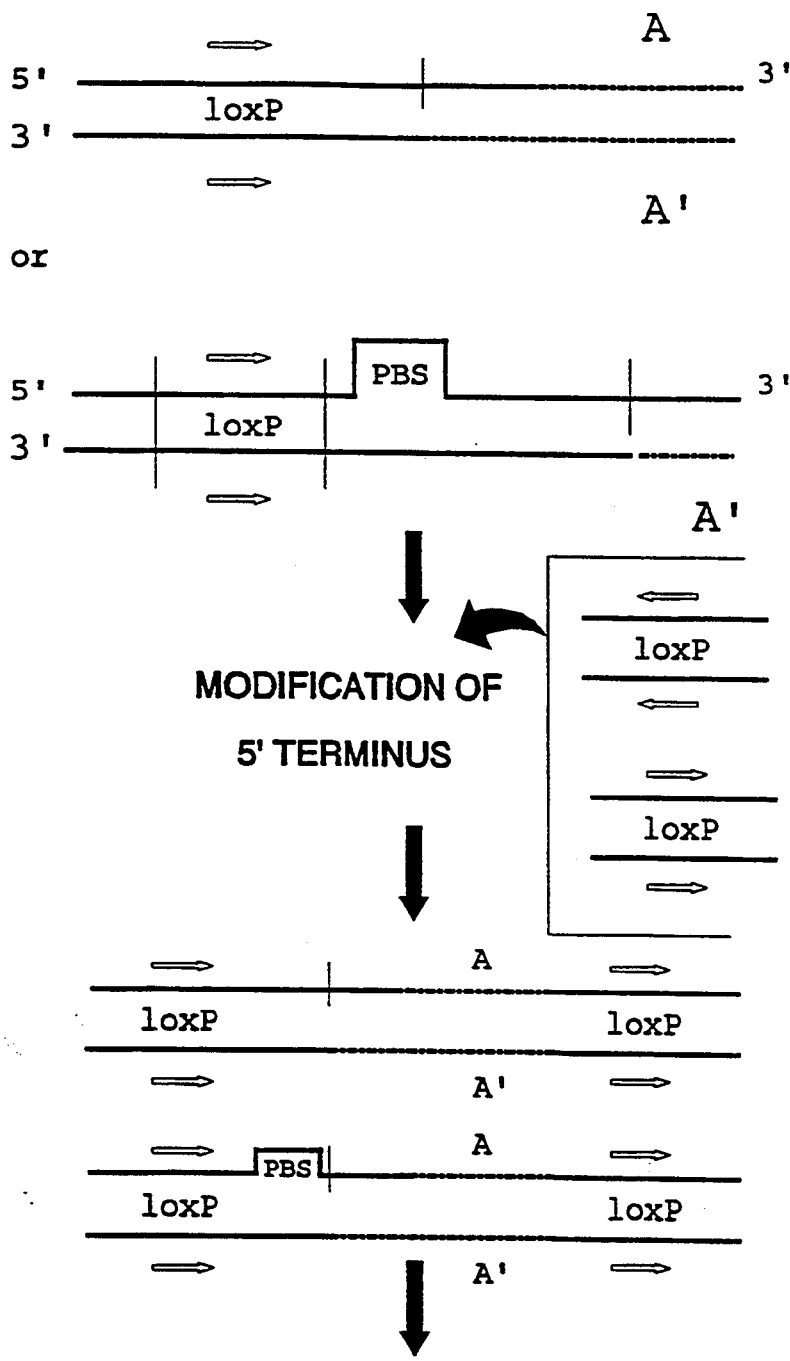
Figure 4D:
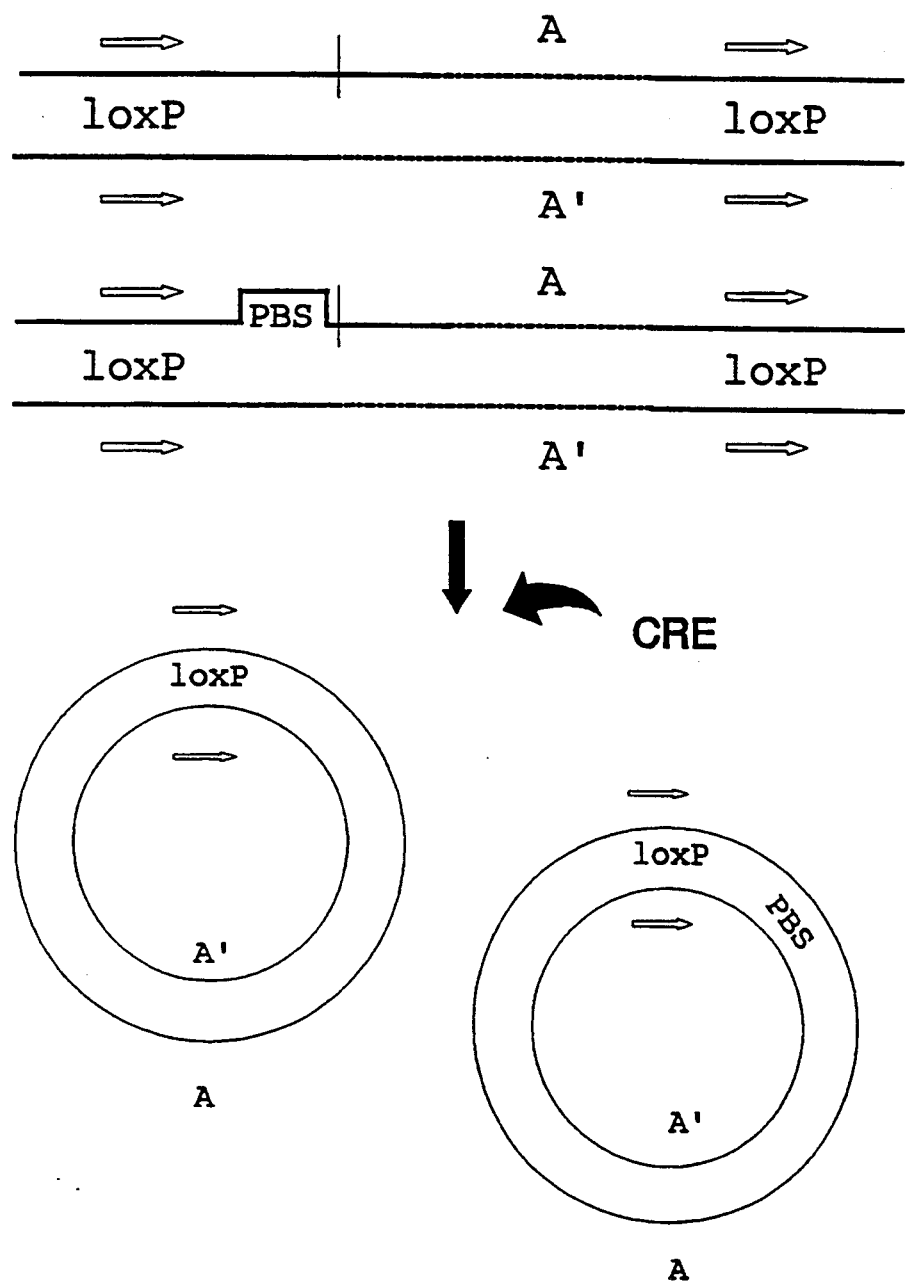

In a first and preferred embodiment employing either the partially single-stranded/partially double-stranded 3' adaptor molecule(s) or the single-stranded 3' adaptor molecule(s), the adaptation of the 3' terminus of the primer extension product is accomplished through the further template-mediated extension of the primer extension products (FIG. 3, lines A, B, C). Most preferably, the adaptor molecules used in this embodiment will contain blocked 3' termini.

In this embodiment, the primer extension products, which have been rendered single-stranded, are permitted to hybridize to the adaptor molecules. As indicated above, the molecules have regions of homology sufficient to permit the primer extension products to hybridize to the adaptor molecule.

Regardless of which type of adaptor molecule(s) is employed, the further extension of the primer extension products results in the formation of a partially-double-stranded and partially single stranded molecule. The molecule is characterized in possessing a protruding 5' terminus whose sequence comprises that of the primer extension product. If the adaptor molecule was partially double-stranded, the further extension of the primer extension product causes the displacement or destruction of the strand that was initially complementary to the template.

2) Ligation

In a second embodiment, to be used when the partially single-stranded/partially double-stranded 3' adaptor molecule(s) of the present invention is employed, the adaptation of the 3' terminus of the primer extension product is accomplished by the ligation of the primer extension molecule to the 3' adaptor molecule (FIG. 3, line D). Because of the complementarity between the sequence of the protruding 3' terminus of the adaptor molecule and the 5' terminus of the primer extension molecule, the two molecules can hybridize to one another. Since the primer extension reaction has been controlled so that the average extension product terminates at a length corresponding to the end of the third region of the desired molecule, the average primer extension product will have a 5' terminus that can hybridize to the adaptor molecule.

When the adaptor molecule is DNA, any DNA ligase may be used to accomplish the ligation of the strands. Significantly, primer extension products that are longer or shorter than the precise length needed to permit the recessed 5' terminus of the adaptor to abut the 3' terminus of the primer extension are not amplified by the methods of the invention. They need not be removed from the reaction, and do not interfere with the subsequent desired amplification.

When the adaptor molecule is a DNA/RNA hybrid (in which the strand having the protruding 3' terminus is RNA), T4 ligase is employed to ligate the DNA strands together (Lehman, I. R., *Science* 186:790–797 (1974); Olivers, B. M. et al., *J. Molec. Biol.* 26:261 (1968); Kleppe, K. et al., *Proc. Natl. Acad. Sci. (U.S.A.)* 67:68 (1970); Fareed, G. C. et al., *J. Biol. Chem.* 246:925 (1971); Sgaramella, V. et al., *Proc. Natl. Acad. Sci. (U.S.A.)* 67:1468 (1970)).

The primer molecules will also have been modified to contain a recombinational site at their 5' terminus as discussed above. Such modification may be performed prior to or after the primer extension of the first or second steps of the method. If the modification is performed by ligation using a single-stranded molecule, the modification is performed prior to the third step of the process. If the modification is performed by ligation using a double-stranded molecule, the modification is performed after the 5' terminus of the primer extension product has been rendered double-stranded.

C. The Third Step of the Methods: Adaptation of the 5' Terminus of the Primer Extension Product Where the 5' terminus of the above-described primer was not initially modified to contain a DNA sequence that, when present in a double-stranded form comprises a recombinational site, such a sequence or site is added to the molecule produced after modification by the above-described 3' adaptor molecules.

1) The Methods Wherein the 3' Adaptor Molecule Comprises a Recombinational Site In the embodiment wherein the 3' adaptor molecule comprises a recombinational site, it is important that the orientation of that site be the same as the orientation of the recombinational site that is to adapt, or has adapted, the 5' terminus of the primer or primer extension product.

In this embodiment of the methods of the invention, illustrated in FIG. 4, the single-stranded adaptor molecule (if that 3' terminus adaptor molecule was used), or the strand of the above-described partially single-stranded and partially double-stranded adaptor molecule that possesses the protruding 3' terminus (if that 3' terminus adaptor molecule was used) is not removed, and is extended by a DNA polymerase to form a double stranded linear DNA molecule having termini that comprise recombinational sites (in direct orientation, if loxP sites). Preferably, the use of a primer binding site in the adaptor molecule will create a "bubble" of single-stranded region located between the recombinational sites.

Action by a recombinase on the recombinational sites yields a double-stranded circular molecule. If the molecule contains the described primer binding site, then such site will provide a single-stranded region which may be used to initiate the replication of the circular molecule.

In one embodiment, such replication leads to a $\theta$ replicon. In a preferred embodiment, the double-stranded circle is "nicked" in one strand to permit a "rolling circle" replicon to form.

Figure 5:
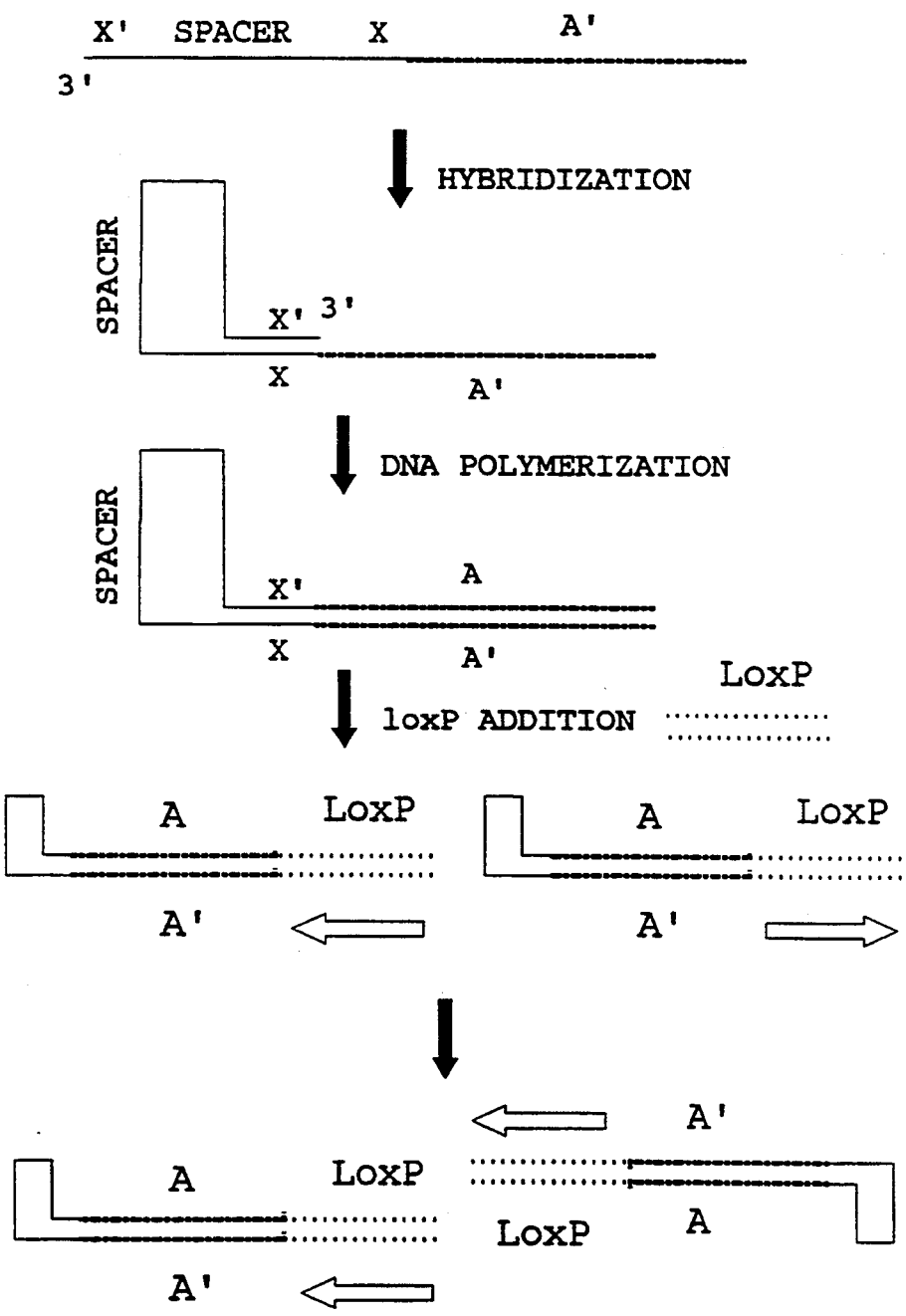
FIG. 5 shows the formation of hairpin loop molecules from the adaptation of the primer extension product with a 3' adaptor molecule having an inverted repeated sequence.

2) The Methods Wherein the 3' Adaptor Molecule Comprises an Inverted Repeated Sequence In the embodiment wherein the 3' adaptor molecule comprises an inverted repeated sequence (FIG. 5), the strand of the adaptor molecule that contained the "protruding 3' terminus" is separated from the primer extension strand. Any means known in the art may be used to accomplish such separation. Optionally, and preferably, the strand of the adaptor molecule that contained the "protruding 3' terminus" is removed from the sample. In a less preferred embodiment, the strand of the adaptor molecule that contained the "protruding 3' terminus" is labelled with biotin. In this embodiment, the sample is heated to denature double-stranded molecules and treated with a biotin-binding agent (for example, streptavidin) to thereby separate or remove the biotinylated molecule from the primer extension product.

In the most preferred embodiment, the strand of the adaptor molecule that contained the "protruding 3' terminus" is RNA, and is separated or removed from primer extension product through the enzymatic activity of RNAse H, which preferentially degrades the RNA strand of an RNA/DNA hybrid.

The reaction conditions are then adjusted, if necessary, to permit DNA polymerization to occur. DNA polymerase is added, if needed, to the reaction, along with nucleotide triphosphates, etc., such that template-dependent extension of the 3' terminus of the adapted molecules can occur.

Since the adaptor molecule contains an inverted repeat, such polymerization results in the formation of a hairpin loop structure. In a preferred mode of the invention, the adaptation of the 5' terminus of the extension product is accomplished after such hairpin loop structures have formed, by providing double-stranded recombinational sites to the reaction, and permitting such sites to ligate to the terminus of the hairpin. This mode of adaptation is preferred, since the ligation of such molecules will occur in a randomized orientation, such that, on average one-half of the molecules will contain recombinational sites that are in one orientation, and one-half of the molecules will contain recombinational sites that are in the opposite orientation.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin origin "rolling circle" replicon manner as described below.

Figure 6:
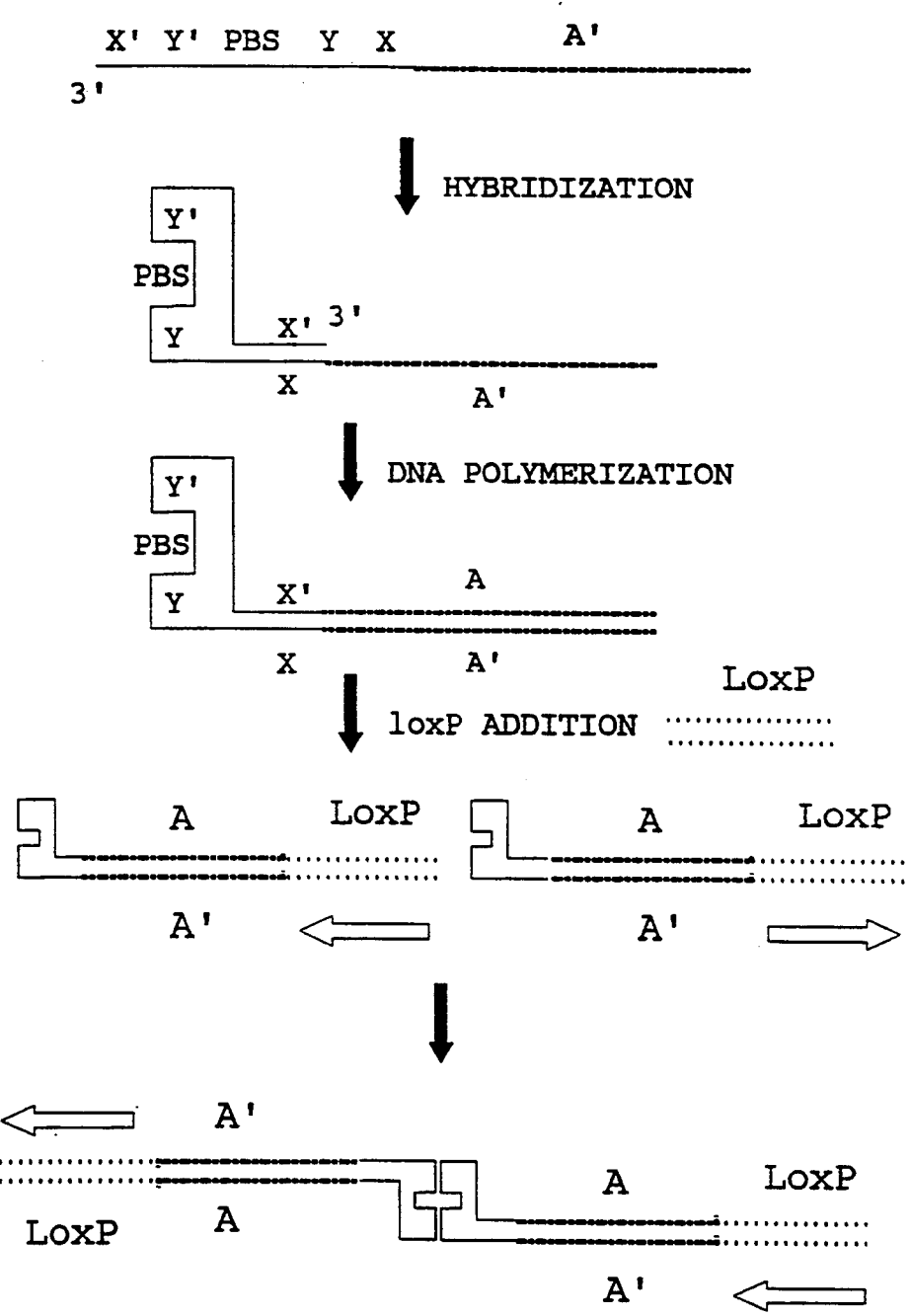
FIG. 6 shows the formation of "bow-tie" molecules from the adaptation of the primer extension product with a 3' adaptor molecule having a pair of nested inverted repeated sequences.

3) The Methods Wherein the 3' Adaptor Molecule Comprises a Pair of Nested Inverted Repeated Sequences In the embodiment wherein the 3' adaptor molecule comprises a pair of nested inverted repeated sequences (FIG. 6), the strand of the adaptor molecule that contained the "protruding 3' terminus" is separated from the primer extension strand, in the manner described above.

The reaction conditions are then adjusted, if necessary, to permit DNA hybridization to occur. The random hybridization of the primer extension products will also result in the formation of a double-stranded molecule having different external inverted repeated sequences (i.e. formed from different 3' adaptor molecules, having different external inverted repeated sequences such as are depicted as X/X' and Q/Q'). The strands of these molecules will anneal to one another due to hybridization between their respective internal inverted repeated sequences. Because the external inverted repeated sequences of the two strands are not complementary to one another, they will not hybridize to one another. Thus, the external repeated sequences of each strand will be able to participate in intra-strand hybridization.

After permitting such hybridization, DNA polymerase is added, if needed, to the reaction, along with nucleotide triphosphates, etc., such that template dependent extension of the 3' terminus of the adapted molecules can occur. The action of DNA polymerase on these molecules will lead to the formation of a "bow-tie" molecule characterized in possessing two hairpin loops that are annealed to one another by virtue of the hybridization between the internal inverted repeated sequences of the molecules.

The terminus of these molecules is then preferably adapted by providing double-stranded recombinational sites to the reaction, and permitting such sites to ligate to the terminus of the hairpin, in the manner described above. Approximately one-half of all bow-tie molecules will contain recombinational sites in direct repeat.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin-origin "rolling circle" manner as described below.

D. The Fourth Step of the Method: Amplification

Because the above steps produce molecules that contain recombinational sites (e.g. loxP), the addition of a recombinase (preferably Cre) catalyzes a double-strand exchange at the recombinational sites of the molecules.

Figure 7:
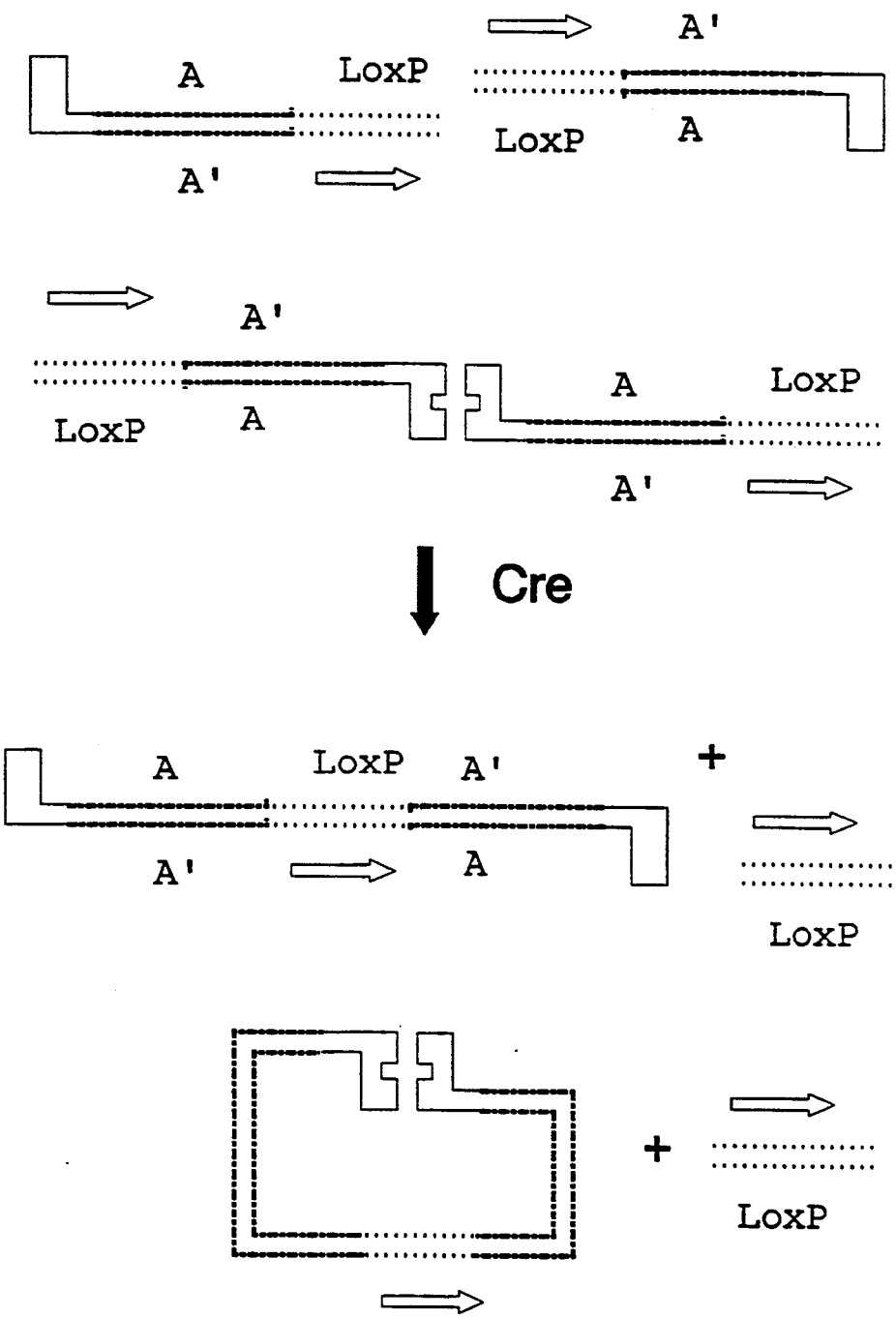
FIG. 7 shows the conversion of hairpin loop and "bow-tie" molecules having directly repeated recombinational sites into single strand circular molecules.

For a "bow-tie" molecule having recombinational sites in the same directional orientation, the recombinational action of the recombinase converts the linear molecules into a single strand circular molecule (FIG. 7). Similarly, two hairpin loops having recombinational sites in the same directional orientation can be recombined to form a single strand circular molecule (FIG. 7). These circular molecules are characterized in having two copies of each strand of the desired sequence, four copies of the spacer region (which optionally comprises the described internal inverted repeated sequences), two copies of each of the two external inverted repeated sequences and a single recombinational site (FIG. 7).

Unless the initially employed primer sequences have been removed or destroyed, these sequences will displace the hybridized strands of the circular molecule. Such displacement may be facilitated by thermally denaturing the molecule, if desired. Such sequences may be used to amplify the desired sequence.

Alternatively, amplification may be accomplished by providing a primer that is complementary to the optional primer binding site. Since the circular molecule does not contain any sequence complementary to the primer binding site, such primer molecules can readily access the site and initiate amplification without thermal denaturation.

Figure 8A:
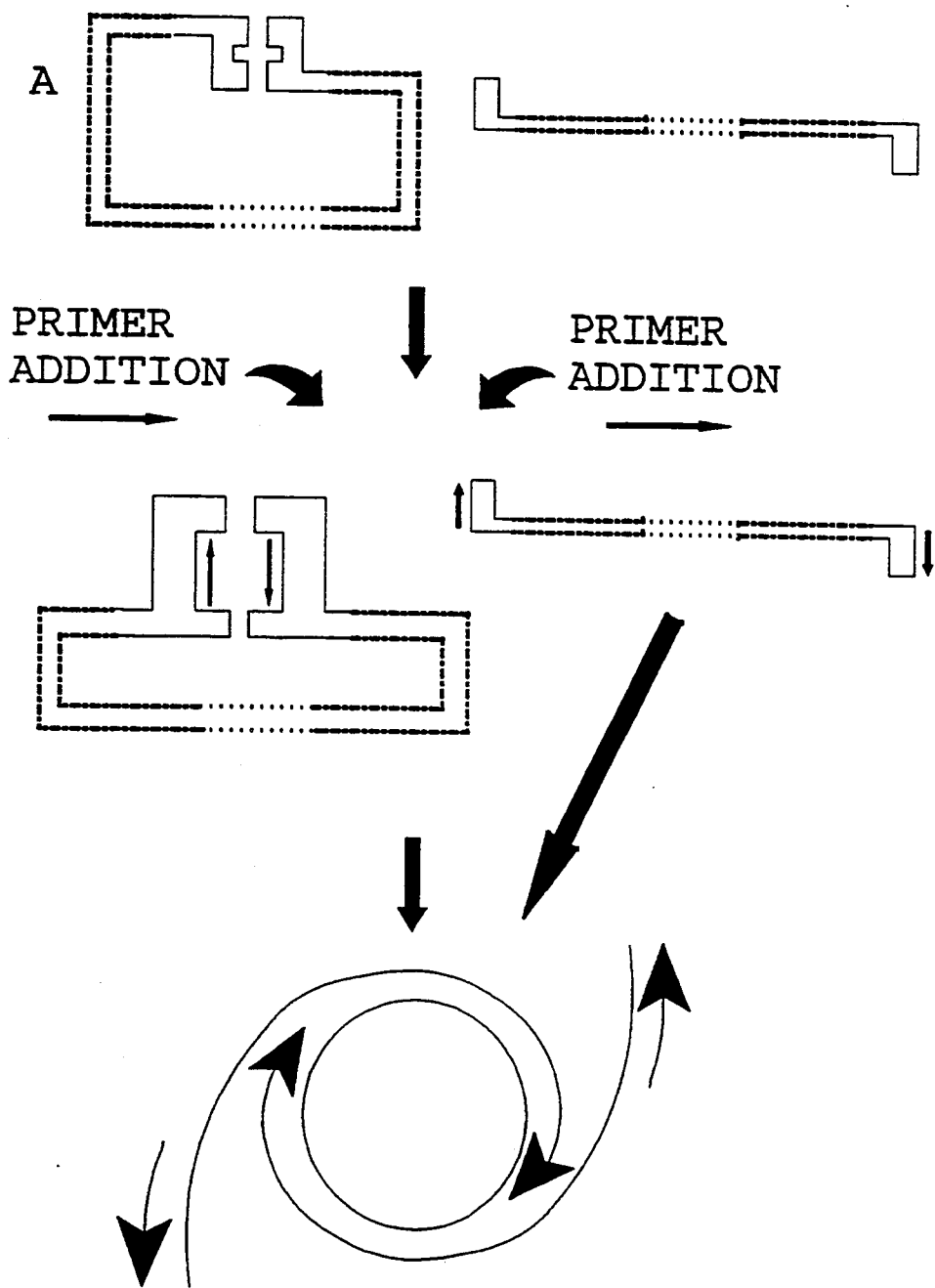
FIG. 8A shows the twin origin "rolling circle" replicon that results from the extension of two primers during the amplification of a single-stranded circular molecule.

For single-stranded circular molecules, since the primers can anneal at two sites on the molecule, primer extension yields a twin-origin "rolling circle" replicon (i.e. a rolling circle replicon having two extending strands, as shown in FIG. 8A).

Figure 8B:
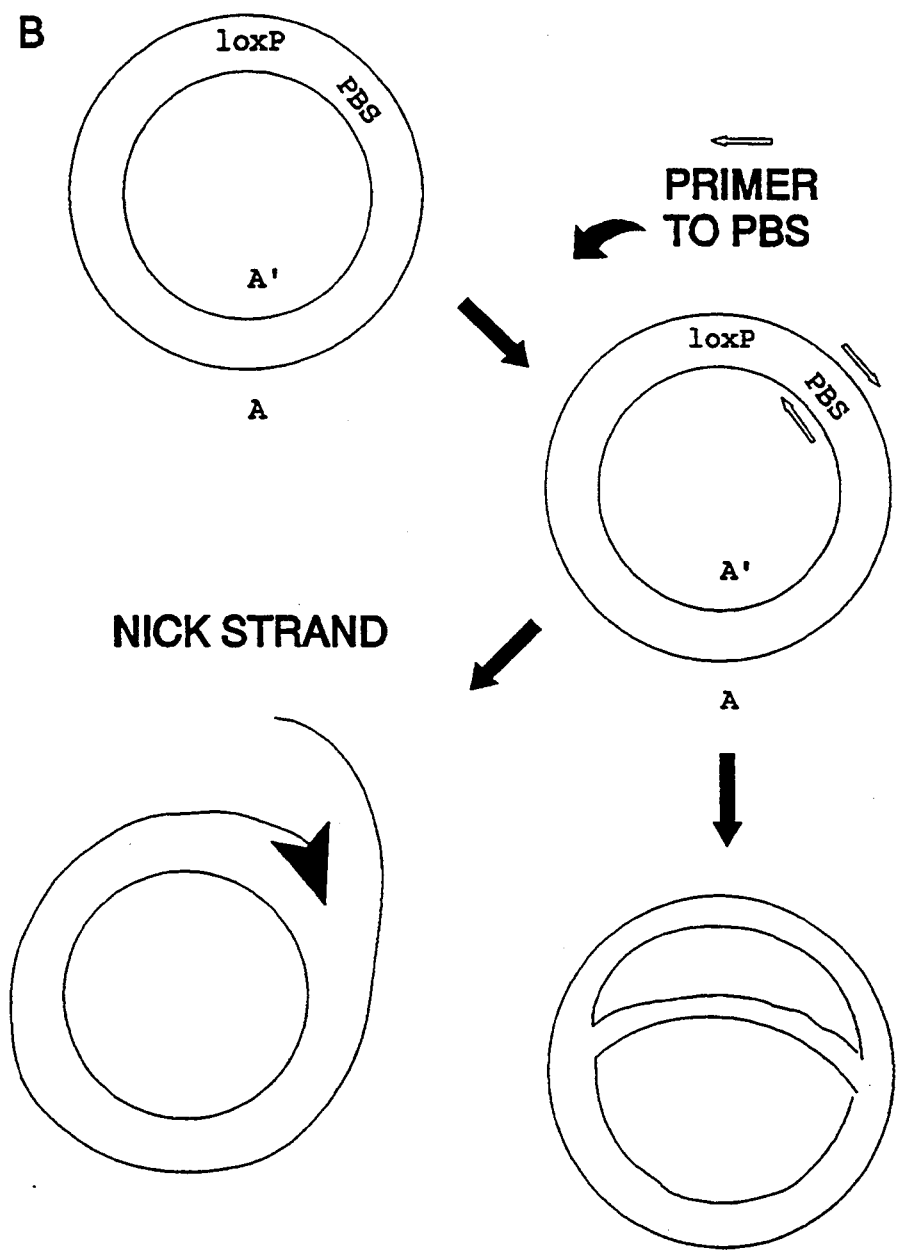
FIG. 8B shows the $\theta$ and "rolling circle" replicons that result from the amplification of a double-stranded circular molecule.

For the double-stranded circular molecules produced by the above method steps, amplification can be preferably obtained in either of two manners. In one embodiment, in which the addition of topoisomerase or gyrase is desirable, the double-stranded molecule is replicated to form a $\theta$ replicon (FIG. 8B). More preferably, one strand of the double-stranded molecule is nicked, such that primer extension results in the displacement of the nicked strand and the formation of a "rolling circle" replicon. Such nicks can be produced by radiation, by chemical adducts (ethidium bromide, etc.), by an endonuclease, or by other means. A preferred method for forming such nicks is by incorporating at least one nucleotide 5'-[α-thio]triphosphate (Pharmacia) into one strand of a restriction site (preferably present in the 3' adaptor molecule). Cleavage at that site by the relevant restriction endonuclease will create a single-strand nick (Walker, G. T. et al., *Proc. Natl. Acad. Sci. (U.S.A.)* 89:392–396 (1992)).

As each strand of any of the above replicons is extended, it provides additional template binding sites for additional primer extension. Thus, the kinetics of amplification are similar to, but faster than, viral burst kinetics.

The presence of inverted repeated sequences and recombinational sites permits additional hairpin loop structures to form. Since the reaction contains Cre, it will mediate recombination between such additional hairpin loop structures to form additional circular structures, thus increasing the number of amplification foci in the reaction.

All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as the replacement of reactants. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased many-fold.

E. Isolation or Purification of the Amplified Molecules

This invention may be combined with many other processes in the arts of molecular biology to achieve a specific end. Of particular interest is purifying the target sequence from the other sequences in the nucleic acid sample. This can be accomplished most advantageously by annealing the nucleic acid sample to an oligonucleotide that is complementary to the target and is immobilized on a solid support. A convenient support would be a microbead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation. Particularly advantageous in some situations is the capture of RNA amplification products by a DNA oligonucleotide complementary to an RNA sequence determined by the target sequence, the oligonucleotide being bound to a solid support such as a magnetic micro-bead. Preferably, this oligonucleotide's sequence does not overlap with that of any oligonucleotide used to purify the target before the amplification. RNA:DNA hybrids thus formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Since the molecules that are being amplified comprise both strands of the desired sequence, the use of restriction endonucleases can cleave the reaction products into discrete and defined fragments. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

The present invention includes articles of manufacture, such as "kits." In one embodiment, such kits will, typically, be specially adapted to contain in close compartmentalization a first container which contains a double-stranded nucleic acid molecule comprising a recombinational site, and a second container which contains a partially single-stranded, partially double-stranded nucleic acid molecule, or a single-stranded nucleic acid molecule, capable of adapting the 3' terminus to produce a hairpin loop that can be extended to form a terminus that is capable of being ligated to the nucleic acid molecule of the first container, and, optionally, a third containing a recombinase suitable for catalyzing the recombination of the sequence of the first container which. The kit may also, optionally, contain one or more DNA and/or RNA polymerases, ligase, buffers, etc. in amounts sufficient to permit the amplification of a desired nucleic acid molecule. The kit may additionally contain instructional brochures, and the like.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A kit, containing:

first container which contains either:
  i) a nucleic acid molecule comprising a single-stranded oligonucleotide which in double-stranded form would comprise a loxP recombinational site, or
  ii) a nucleic acid molecule whose sequence comprises a LoxP recombinational site;
a second container which contains either:
  i) a double-stranded nucleic acid molecule having a double-stranded region and a single-stranded protruding 3' region, wherein said double-stranded region comprises an inverted repeat oligonucleotide, and optionally contains a spacer oligonucleotide between the termini of the inverted repeat, said inverted repeat oligonucleotide being of sufficient length to permit said nucleic acid molecule to form a recessed 3' terminus from the intra-strand hybridization of said inverted repeat oligonucleotide; or
  ii) a single-stranded nucleic acid molecule, wherein said molecule comprises an inverted repeat oligonucleotide optionally containing a spacer oligonucleotide between the termini of the inverted repeat, said inverted repeat oligonucleotide being of sufficient length to permit said nucleic acid molecule to form a recessed 3' terminus from the intra-strand hybridization of said inverted repeat oligonucleotide;
and a third container containing a Cre recombinase suitable for catalyzing the recombination of the recombinational site sequence of the first container.

2. A method for amplifying a desired polynucleotide of a target nucleic acid molecule, said polynucleotide having a 3' region, said method comprising the steps:
  A) incubating said target molecule in the presence of a primer nucleic acid molecule and a polymerase; hybridizing said primer molecule to said 3' region of said desired polynucleotide and subsequently forming primer extension products that each have a 3' terminus;
  B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing an inverted repeat oligonucleotide; said inverted repeat oligonucleotide optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;
  C) ligating said hybridized 3' terminus of said primer extension products of step B to the second strand of said double-stranded nucleic acid molecules of step B, thereby joining said inverted repeat oligonucleotide to said primer extension product;
  D) incubating said ligated primer extension products of step C under conditions sufficient to permit said intra-strand hybridization between the termini of said inverted repeat oligonucleotide, thereby yielding nucleic acid molecules having a recessed, hybridized 3' terminus;
  E) permitting template-dependent extension of said recessed 3' terminus of said molecules of step D to thereby form single-stranded nucleic acid molecules having a single 3' and a single 5' terminal sequence and a double-stranded region between said terminal sequences;
  F) ligating a LoxP recombinational site to said 3' terminus and said 5' terminus of the molecules of step E;
  G) incubating said molecules from step F in the presence of a Cre recombinase under conditions sufficient to form an amplifiable circular molecule containing said desired polynucleotide due to LoxP site-specific recombination between two of said molecules; and
  H) incubating said amplifiable circular molecules in the presence of an amplification primer under conditions sufficient to permit the template-dependent extension of said primer, said extension thereby amplifying said desired polynucleotide.

3. The method of claim 2, wherein said inverted repeat oligonucleotide contains said spacer oligonucleotide, and wherein said spacer oligonucleotide comprises a primer binding site.

4. A method for amplifying a desired polynucleotide of a target nucleic acid molecule, said polynucleotide having a 3' region, said method comprising the steps:
  A) incubating said target molecule in the presence of a primer nucleic acid molecule and a polymerase; hybridizing said primer molecule to said 3' region of said desired polynucleotide and subsequently forming primer extension products that each have a 3' terminus;
  B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing an inverted repeat oligonucleotide; said inverted repeat oligonucleotide optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;
  C) extending the 3' terminus of said hybridized primer extension products in a template-dependent, polymerase-mediated reaction such that a further extended primer extension product is produced that contains said inverted repeat oligonucleotide;
  D) incubating said further extended primer extension products of step C under conditions sufficient to permit intra-strand hybridization of the termini of said inverted repeat oligonucleotide, thereby yielding nucleic acid molecules having a recessed, hybridized 3' terminus;
  E) permitting template-dependent extension of said recessed 3' terminus of said molecules of step D to thereby form single-stranded nucleic acid molecules having a single 3' and a single 5' terminal sequence and a double-stranded region between said terminal sequences;
  F) ligating a LoxP recombinational site to said 3' terminus and said 5' terminus;
  G) incubating said molecules from step F in the presence of a Cre recombinase under conditions sufficient to form an amplifiable circular molecule containing said desired polynucleotide due to LoxP site-specific recombination between two of said molecules; and H) incubating said amplifiable circular molecules in the presence of an amplification primer under conditions sufficient to permit the template-dependent extension of said primer, said extension thereby amplifying said desired polynucleotide.

5. The method of claim 4, wherein said inverted repeat oligonucleotide contains said spacer oligonucleotide, and wherein said spacer oligonucleotide comprises a primer binding site.

6. A method for amplifying a desired polynucleotide of a target nucleic acid molecule, said polynucleotide having a 3' region, said method comprising the steps:

A) incubating said target molecule in the presence of a primer nucleic acid molecule and a polymerase; hybridizing said primer molecule to said 3' region of said desired polynucleotide and subsequently forming primer extension products that each have a 3' terminus;

B) hybridizing the 3' terminus of a primer extension product of step A to a 3' region of a single-stranded nucleic acid molecule having: (i) said 3' region and (ii) an inverted repeat oligonucleotide; said inverted repeat oligonucleotide being located at a position 5' to said 3' region and optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;

C) extending the 3' terminus of said hybridized primer extension products in a template-dependent, polymerase-mediated reaction such that a further extended primer extension product is produced that contains said inverted repeat oligonucleotide;

D) incubating said further extended primer extension products of step C under conditions sufficient to permit intra-strand hybridization between the termini of said inverted repeat oligonucleotide, thereby yielding nucleic acid molecules having a recessed, hybridized 3' terminus;

E) permitting template-dependent extension of said recessed 3' terminus of said molecules of step D to thereby form single-stranded nucleic acid molecules having a single 3' and a single 5' terminal sequence and a double-stranded region between said terminal sequences;

F) ligating a LoxP recombinational site to said 3' terminus and said 5' terminus;

G) incubating said molecules from step F in the presence of a Cre recombinase under conditions sufficient to form an amplifiable circular molecule containing said desired polynucleotide due to LoxP site-specific recombination between two of said molecules; and H) incubating said amplifiable circular molecules in the presence of an amplification primer under conditions sufficient to permit the template-dependent extension of said primer, said extension thereby amplifying said desired polynucleotide.

7. The method of claim 6, wherein said inverted repeat oligonucleotide contains said spacer oligonucleotide, and wherein said spacer oligonucleotide comprises a primer binding site.

8. A method for amplifying a desired polynucleotide of a target nucleic acid molecule, said polynucleotide having a 3' region, said method comprising the steps:

A) incubating said target molecule in the presence of a primer nucleic acid molecule and a polymerase; wherein the 5' terminus of said primer contains an oligonucleotide, which, in double-stranded form comprises a LoxP recombinational site; hybridizing said primer molecule to said 3' region of said desired polynucleotide; and subsequently forming primer extension products that each have a 3' terminus;

B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing an inverted repeat oligonucleotide; said inverted repeat oligonucleotide optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;

C) ligating said hybridized 3' terminus of said primer extension products of step B to the second strand of said double-stranded nucleic acid molecules of step B, thereby joining said inverted repeat oligonucleotide to said primer extension product;

D) incubating said ligated primer extension products of step C under conditions sufficient to permit said intra-strand hybridization between the termini of said inverted repeat oligonucleotide, thereby yielding nucleic acid molecules having a recessed, hybridized 3' terminus;

E) permitting template-dependent extension of said recessed 3' terminus of said molecules of step D to thereby form single-stranded nucleic acid molecules having a single 3' and a single 5' terminal sequence and a double-stranded region between said terminal sequences, and containing a double-stranded LoxP recombinational site;

F) incubating said molecules from step E in the presence of a Cre recombinase under conditions sufficient to form an amplifiable circular molecule containing said desired polynucleotide due to LoxP site-specific recombination between two of said molecules; and G) incubating said amplifiable circular molecules in the presence of an amplification primer under conditions sufficient to permit the template dependent extension of said primer, said extension thereby amplifying said desired polynucleotide.

9. The method of claim 8, wherein said inverted repeat oligonucleotide contains said spacer oligonucleotide, and wherein said spacer oligonucleotide comprises a primer binding site.

10. A method for amplifying a desired polynucleotide of a target nucleic acid molecule, said polynucleotide having a 3' region, said method comprising the steps:

A) incubating said target molecule in the presence of a primer nucleic acid molecule and a polymerase; wherein the 5' terminus of said primer contains an oligonucleotide, which, in double-stranded form comprises a LoxP recombinational site; hybridizing said primer molecule to said 3' region of said desired polynucleotide and subsequently forming primer extension products that each have a 3' terminus;

B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing an inverted repeat oligonucleotide; said inverted repeat oligonucleotide optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;

C) extending the 3' terminus of said hybridized primer extension products in a template-dependent, polymerase-mediated reaction such that a further extended primer extension product is produced that contains an inverted repeat oligonucleotide;

D) incubating said further extended primer extension products of step C under conditions sufficient to permit intra-strand hybridization of the termini of said inverted repeat oligonucleotide, thereby yielding nucleic acid molecules having a recessed, hybridized 3' terminus;

E) permitting template-dependent extension of said recessed 3' terminus of said molecules of step D to thereby form single-stranded nucleic acid molecules having a single 3' and a single 5' terminal sequence and a double-stranded region between said terminal sequences, and containing a double-stranded LoxP recombinational site;

F) incubating said molecules from step E in the presence of a Cre recombinase under conditions sufficient to form an amplifiable circular molecule containing said desired polynucleotide due to LoxP site-specific recombination between two of said molecules; and G) incubating said amplifiable circular molecules in the presence of an amplification primer under conditions sufficient to permit the template dependent extension of said primer, said extension thereby amplifying said desired polynucleotide.

11. The method of claim 10, wherein said inverted repeat oligonucleotide contains said spacer oligonucleotide, and wherein said spacer oligonucleotide comprises a primer binding site.

12. A method for amplifying a desired polynucleotide of a target nucleic acid molecule, said polynucleotide having a 3' region, said method comprising the steps:

A) incubating said target molecule in the presence of a primer nucleic acid molecule and a polymerase; wherein the 5' terminus of said primer contains an oligonucleotide, which, in double-stranded form comprises a LoxP recombinational site; hybridizing said primer molecule to said 3' region of said desired polynucleotide and subsequently forming primer extension products that each have a 3' terminus;

B) hybridizing the 3' terminus of a primer extension product of step A to a 3' region of a single-stranded nucleic acid molecule having (i) said 3' region and (ii) an inverted repeat oligonucleotide; said inverted repeat oligonucleotide being located at a position 5' to said 3' region and optionally containing a spacer oligonucleotide between the termini of the inverted repeat; said inverted repeat oligonucleotide being of sufficient length to permit said nucleic acid molecule to form a recessed 3' terminus from the intra-strand hybridization of said inverted repeat oligonucleotide;

C) extending the 3' terminus of said hybridized primer extension products in a template-dependent, polymerase-mediated reaction such that a further extended primer extension product is produced that contains an inverted repeat oligonucleotide;

D) incubating said further extended primer extension products of step C under conditions sufficient to permit intra-strand hybridization of the termini of said inverted repeat oligonucleotide, thereby yielding nucleic acid molecules having a recessed, hybridized 3' terminus;

E) permitting template-dependent extension of said recessed 3' terminus of said molecules of step D to thereby form single-stranded nucleic acid molecules having a single 3' and a single 5' terminal sequence and a double-stranded region between said terminal sequences, and containing a double-stranded LoxP recombinational site;

F) incubating said molecules from step E in the presence of a Cre recombinase under conditions sufficient to form an amplifiable circular molecule containing said desired polynucleotide due to LoxP site-specific recombination between two of said molecules; and G) incubating said amplifiable circular molecules in the presence of an amplification primer under conditions sufficient to permit the template dependent extension of said primer, said extension thereby amplifying said desired polynucleotide.

13. The method of claim 12, wherein said inverted repeat oligonucleotide contains said spacer oligonucleotide, and wherein said spacer oligonucleotide comprises a primer binding site.

14. A method for amplifying a desired polynucleotide of a target nucleic acid molecule, said polynucleotide having a 3' region, said method comprising the steps:

A) incubating said target molecule in the presence of a primer nucleic acid molecule and a polymerase; hybridizing said primer molecule to said 3' region of said desired polynucleotide and subsequently forming primer extension products that each have a 3' terminus;

B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing a LoxP site;

D) ligating said hybridized 3' terminus of said primer extension products to a 5' terminus of said second strand of said double-stranded molecule; permitting template dependent extension of said 3' terminus of said hybridized first strand; to thereby form linear double-stranded nucleic acid molecules having LoxP recombinational sites at both termini, said sites having a directly repeated orientation with respect to one another;

D) incubating said molecules from step C in the presence of a Cre recombinase under conditions sufficient to form a double-stranded amplifiable circular molecule containing said desired polynucleotide due to LoxP site-specific recombination between the LoxP recombinational sites of the two termini of said molecules;

E) incubating said double-stranded amplifiable circular molecules in the presence of an amplification primer under conditions sufficient to permit the template dependent extension of said primer, said extension thereby amplifying said desired polynucleotide.

15. The method of claim 14, wherein in step E, one strand of said double-stranded amplifiable circular molecules is cleaved and one strand is circular, and wherein in said incubation said amplification primer is hybridized to said circular strand.

16. The method of claim 15, wherein said amplification primer has a nucleotide sequence sufficient to permit said molecule to hybridize to either strand of said double-stranded circular molecule.

17. A method for amplifying a desired polynucleotide of a target nucleic acid molecule, said polynucleotide having a 3' region, said method comprising the steps:
A) incubating said target molecule in the presence of a primer nucleic acid molecule and a polymerase; hybridizing said primer molecule to said 3' region of said desired polynucleotide and subsequently forming primer extension products that each have a 3' terminus;
B) hybridizing the 3' terminus of a primer extension product of step A to a protruding 3' single-stranded region of a first strand of a double-stranded nucleic acid molecule having: (i) said single-stranded protruding 3' region and (ii) a double-stranded region consisting of said first strand and a second strand, said double-stranded region containing a LoxP site;
D) permitting template-dependent extension of said hybridized 3' terminus of said primer extension products; permitting template-dependent extension of said 3' terminus of said hybridized first strand; to thereby form linear double-stranded nucleic acid molecules having LoxP recombinational sites at both termini, said sites having a directly repeated orientation with respect to one another;
D) incubating said molecules from step C in the presence of a Cre recombinase under conditions sufficient to form a double-stranded amplifiable circular molecule containing said desired polynucleotide due to LoxP site-specific recombination between the LoxP recombinational sites of the two termini of said molecules;
E) incubating said double-stranded amplifiable circular molecules in the presence of an amplification primer under conditions sufficient to permit the template dependent extension of said primer, said extension thereby amplifying said desired polynucleotide.

18. The method of claim 17, wherein in step E, one strand of said double-stranded amplifiable circular molecules is cleaved and one strand is circular, and wherein in said incubation said amplification primer is hybridized to said circular strand.

19. The method of claim 18, wherein said amplification primer has a nucleotide sequence sufficient to permit said molecule to hybridize to either strand of said double-stranded circular molecule.

20. A method for amplifying a desired polynucleotide of a target nucleic acid molecule, said polynucleotide having a 3' region, said method comprising the steps:
A) incubating said target molecule in the presence of a primer nucleic acid molecule and a polymerase; wherein the 5' terminus of said primer contains an oligonucleotide, which, in double-stranded form comprises a LoxP recombinational site; hybridizing said primer molecule to said 3' region of said desired polynucleotide and subsequently forming primer extension products that each have a 3' terminus;
B) hybridizing the 3' terminus of a primer extension products of step A to a 3' terminus of single-stranded nucleic acid molecules having an oligonucleotide, which, in double-stranded form comprises a LoxP recombinational site; said oligonucleotide being located at a position 5' to said molecule's 3' terminus;
C) permitting template dependent extension of said hybridized 3' terminus of said primer extension products and of said hybridized 3' terminus of said single-stranded molecules of step B to thereby form linear double-stranded nucleic acid molecules having LoxP recombinational sites at both termini, said sites having a directly repeated orientation with respect to one another;
D) incubating said molecules from step C in the presence of a Cre recombinase under conditions sufficient to form a double-stranded amplifiable circular molecule containing said desired polynucleotide due to LoxP site-specific recombination between the LoxP recombinational sites of the two termini of said molecules;
E) incubating said double-stranded amplifiable circular molecules in the presence of an amplification primer under conditions sufficient to permit the template dependent extension of said primer, said extension thereby amplifying said desired polynucleotide.

21. The method of claim 20, wherein in step E, one strand of said double-stranded amplifiable circular molecules is cleaved and one strand is circular, and wherein in said incubation said amplification primer is hybridized to said circular strand.

22. The method of claim 21, wherein said amplification primer has a nucleotide sequence sufficient to permit said molecule to hybridize to either strand of said double-stranded circular molecule.

* * * * *